US009318029B2

(12) United States Patent
Katz et al.

(10) Patent No.: US 9,318,029 B2
(45) Date of Patent: Apr. 19, 2016

(54) RESPONSE SCORING SYSTEM FOR VERBAL BEHAVIOR WITHIN A BEHAVIORAL STREAM WITH A REMOTE CENTRAL PROCESSING SYSTEM AND ASSOCIATED HANDHELD COMMUNICATING DEVICES

(75) Inventors: Barry Katz, Flushing, NY (US); Robert Peterson, Houston, NY (US)

(73) Assignee: BARRY KATZ, Flushing, NY (US)

(*) Notice: Subject to any disclaimer, the term of this patent is extended or adjusted under 35 U.S.C. 154(b) by 367 days.

(21) Appl. No.: 13/468,756

(22) Filed: May 10, 2012

(65) Prior Publication Data

US 2012/0329018 A1    Dec. 27, 2012

Related U.S. Application Data

(62) Division of application No. 11/779,738, filed on Jul. 18, 2007, now Pat. No. 8,182,267.

(60) Provisional application No. 60/831,551, filed on Jul. 18, 2006, provisional application No. 60/831,552, filed on Jul. 18, 2006, provisional application No. 60/885,583, filed on Jan. 18, 2007.

(51) Int. Cl.
*G06F 3/00* (2006.01)
*G09B 19/00* (2006.01)
(Continued)

(52) U.S. Cl.
CPC .............. *G09B 19/00* (2013.01); *A61B 3/0066* (2013.01); *A61B 3/113* (2013.01); *A61B 3/145* (2013.01); *A61B 5/1114* (2013.01); *A61B 5/6803* (2013.01); *A61B 5/6821* (2013.01);
(Continued)

(58) Field of Classification Search
CPC ....... G06F 3/011; G06F 3/013; A61B 3/0066; A61B 3/145; A61B 3/04842; A61B 5/1114; A61B 5/6803; A61B 5/6821; A61B 5/7264; G09B 1/00; G09B 5/00; G09B 5/062; G09B 7/00; G09B 19/00; G09B 23/28; G06T 7/004; G06T 11/00; G06T 2207/30201; A63F 2300/8082; G02C 5/001
USPC ................................................. 434/236, 238
See application file for complete search history.

(56) References Cited

U.S. PATENT DOCUMENTS 5,029,216 A * 7/1991 Jhabvala ................. G02C 11/06
381/26
5,596,994 A    1/1997 Bro
(Continued)

OTHER PUBLICATIONS

Wolf, Montrose; Social Validity: The case for subjective measurement or How applied behavior analysis is finding its heart; Journal of Applied Behavior analysis, 1978, 11, 203-214.*

(Continued)

*Primary Examiner* — Nikolai A Gishnock
(74) *Attorney, Agent, or Firm* — Ostrolenk Faber LLP

(57) ABSTRACT

A system, method and related devices for monitoring and improving the training and social eye contact and communication skills of developmentally challenged individuals such as autistic individuals with special needs in improving their interpersonal communicating and other skills. A WatchMe component of the system and method monitors and obtains qualitative and quantitative information about the eye contact habits of a subject being trained or interviewed. It provides stimuli that promotes and encourages improvements in the eye contact habits of the subject.

15 Claims, 29 Drawing Sheets

(51) Int. Cl.
| | |
|---|---|
| G06F 3/01 | (2006.01) |
| A61B 3/113 | (2006.01) |
| A61B 3/00 | (2006.01) |
| A61B 3/14 | (2006.01) |
| A61B 5/11 | (2006.01) |
| A61B 5/00 | (2006.01) |
| G09B 5/06 | (2006.01) |
| G09B 1/00 | (2006.01) |
| G09B 23/28 | (2006.01) |
| G06T 7/00 | (2006.01) |
| G06T 11/00 | (2006.01) |
| G06Q 50/22 | (2012.01) |
| G09B 5/00 | (2006.01) |
| G09B 7/00 | (2006.01) |
| A61B 5/0484 | (2006.01) |
| G02C 5/00 | (2006.01) |

(52) U.S. Cl.
CPC .............. *A61B5/7264* (2013.01); *G06F 3/011* (2013.01); *G06F 3/013* (2013.01); *G06Q 50/22* (2013.01); *G06T 7/004* (2013.01); *G06T 11/00* (2013.01); *G09B 1/00* (2013.01); *G09B 5/00* (2013.01); *G09B 5/062* (2013.01); *G09B 7/00* (2013.01); *G09B 23/28* (2013.01); *A61B 5/04842* (2013.01); *A63F 2300/8082* (2013.01); *G02C 5/001* (2013.01); *G06T 2207/30201* (2013.01)

(56) References Cited

U.S. PATENT DOCUMENTS

| | | | | |
|---|---|---|---|---|
| 5,599,239 A * | 2/1997 | Kim et al. | | 473/208 |
| 5,722,418 A | 3/1998 | Bro | | |
| 5,879,163 A | 3/1999 | Brown et al. | | |
| 6,513,928 B1 * | 2/2003 | Moore | A61F 9/025 | 351/107 |
| 7,063,535 B2 * | 6/2006 | Stamm et al. | | 434/236 |
| 7,515,054 B2 * | 4/2009 | Torch | | 340/573.1 |
| 7,648,326 B2 * | 1/2010 | Santele | E02F 3/36 | 37/468 |
| 7,735,114 B2 | 6/2010 | Kwan et al. | | |
| 7,762,665 B2 * | 7/2010 | Vertegaal | G06F 3/011 | 351/209 |
| 8,096,660 B2 * | 1/2012 | Vertegaal | G06F 3/011 | 351/209 |
| 8,182,267 B2 * | 5/2012 | Katz | G06Q 50/22 | 434/236 |
| 8,292,433 B2 * | 10/2012 | Vertegaal | G06F 3/011 | 351/209 |
| 8,322,856 B2 * | 12/2012 | Vertegaal | G06F 3/011 | 351/209 |
| 8,500,271 B2 * | 8/2013 | Howell | G02C 5/001 | 351/122 |
| 8,543,061 B2 * | 9/2013 | Suhami | G10K 11/1786 | 381/313 |
| 8,596,786 B2 * | 12/2013 | Bublitz | A61B 3/113 | 351/206 |
| 8,672,482 B2 * | 3/2014 | Vertegaal | G06F 3/011 | 351/209 |
| 8,766,765 B2 * | 7/2014 | Hamadallah | G02C 11/10 | 340/4.12 |
| 8,770,742 B2 * | 7/2014 | Howell | G02C 11/00 | 351/158 |
| 8,905,542 B2 * | 12/2014 | Howell | G02C 5/001 | 351/158 |
| 9,144,376 B2 * | 9/2015 | Guth | A61B 3/09 | |
| 2001/0016818 A1 * | 8/2001 | Hara | G10L 21/06 | 704/500 |
| 2002/0140741 A1 | 10/2002 | Felkey et al. | | |
| 2004/0183749 A1 * | 9/2004 | Vertegaal | | 345/7 |
| 2004/0219500 A1 | 11/2004 | Brown et al. | | |
| 2005/0046789 A1 * | 3/2005 | Jannard | G02C 11/06 | 351/158 |
| 2005/0086082 A1 | 4/2005 | Braunstein et al. | | |
| 2006/0003803 A1 * | 1/2006 | Thomas | G02C 11/06 | 455/556.1 |
| 2006/0053036 A1 | 3/2006 | Coffman et al. | | |
| 2006/0206358 A1 | 9/2006 | Beaver | | |
| 2007/0160254 A1 * | 7/2007 | Ritter | G02C 11/06 | 381/381 |
| 2008/0151179 A1 * | 6/2008 | Howell | G02C 11/00 | 351/158 |
| 2010/0110368 A1 * | 5/2010 | Chaum | G02B 27/017 | 351/158 |

OTHER PUBLICATIONS

Search Report issued by PCT on Apr. 23, 2008 in connection with corresponding PCT application No. PCT/US2007/16320.

* cited by examiner

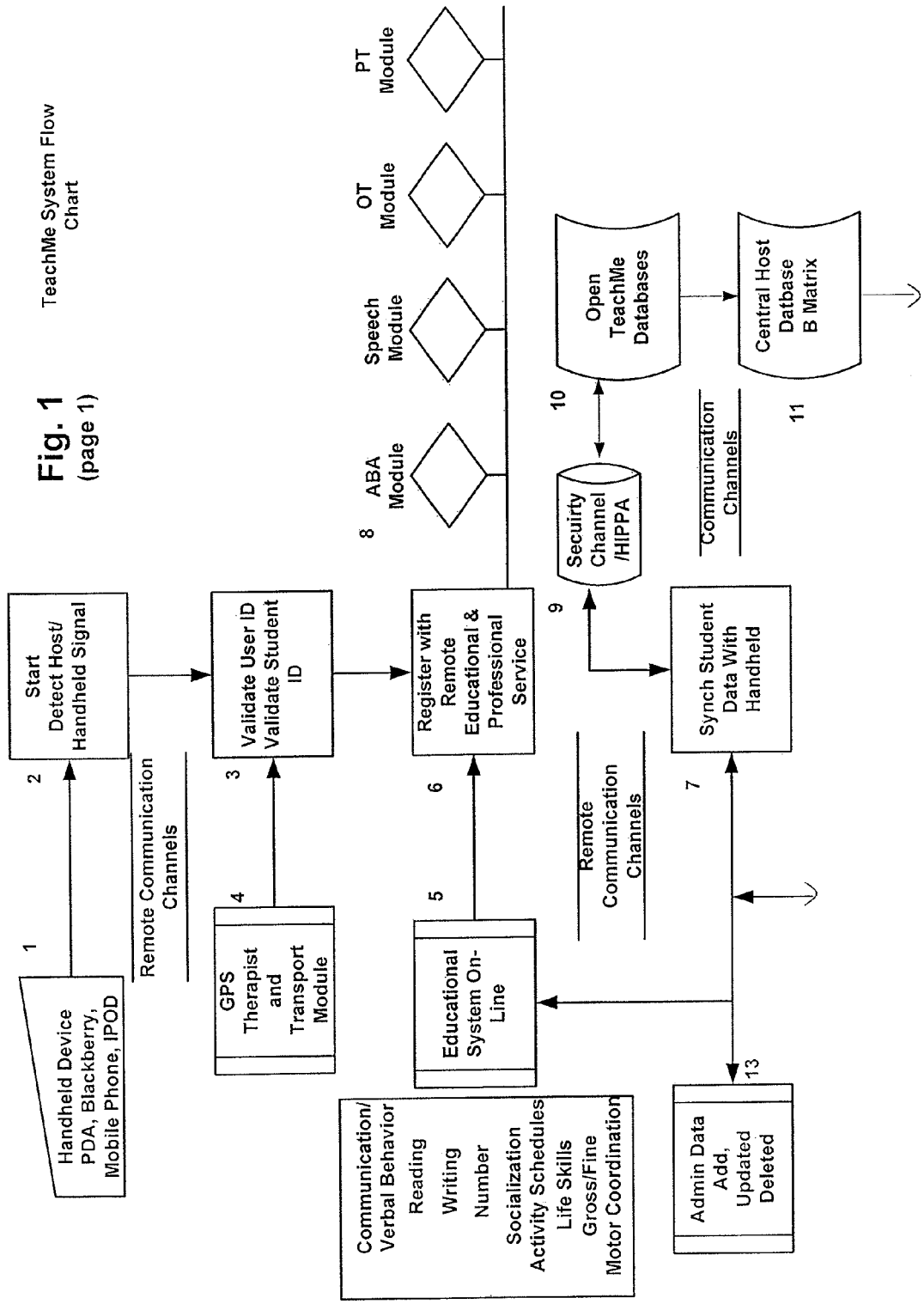

(page 2)

Information Flow Between
B Matrix Defined and Non
B Matrix Undefined

FIG. 4c

| First Name | Short Description | Start | End_Time | NumberCorrectIndependent |
|---|---|---|---|---|
| | NumberInCorrectIndependent | | | |
| Mary | Animal sounds | 1/16/2007 12:45 | 1/16/2007 13:08 | 16 |
| Mary | Animal sounds | 1/16/2007 12:44 | 1/16/2007 12:44 | 18 |
| Mary | Animal sounds | 1/16/2007 12:39 | 1/16/2007 12:39 | 18 |
| Mary | Animal sounds | 1/16/2007 9:08 | 1/16/2007 9:08 | 19 |
| Mary | Fill in blanks re: Fun | 1/16/2007 9:09 | 1/16/2007 9:09 | 0 |
| Mary | Labels common objects | 1/16/2007 8:29 | 1/16/2007 9:06 | 13 |
| Mary | Labels common people. | 1/16/2007 9:06 | 1/16/2007 9:06 | 17 |
| Mary | Labels reinforcers | 1/16/2007 9:06 | 1/16/2007 9:07 | 12 |
| Mary | Uses tissue | 1/16/2007 8:19 | 1/16/2007 8:19 | 6 |

Fig. 4e

Antecedent Audio/Visual Behavior Tracking Component Module

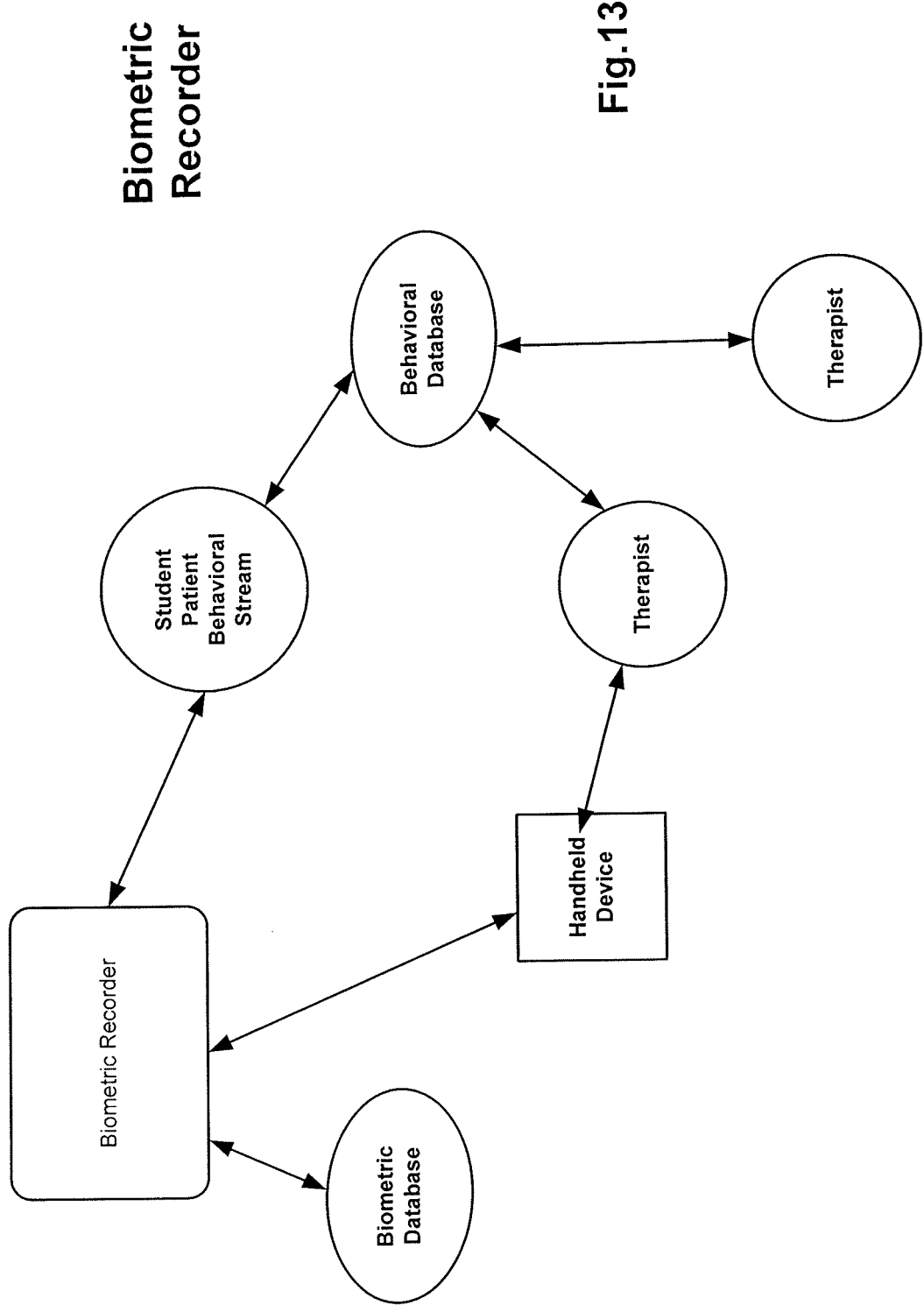

RESPONSE SCORING SYSTEM FOR VERBAL BEHAVIOR WITHIN A BEHAVIORAL STREAM WITH A REMOTE CENTRAL PROCESSING SYSTEM AND ASSOCIATED HANDHELD COMMUNICATING DEVICES

CROSS REFERENCE TO RELATED APPLICATIONS

The present application is a divisional under 37 C.F.R. §1.53(b) of prior application Ser. No. 11/779,738, filed Jul. 18, 2007, by Barry KATZ, et al., entitled A RESPONSE SCORING SYSTEM FOR VERBAL BEHAVIOR WITHIN A BEHAVIORAL STREAM WITH A REMOTE CENTRAL PROCESSING SYSTEM AND ASSOCIATED HANDHELD COMMUNICATING DEVICES, which claims benefit of and priority to: U.S. Provisional Application Ser. No. 60/831,551 filed on Jul. 18, 2006 entitled MONITORING SOCIAL CONTACTS USING A BIDIRECTIONAL SIGNAL DETECTING SYSTEM AND A BEHAVIORAL TRAINING; U.S. Provisional Application Ser. No. 60/831,552 filed on Jul. 18, 2006 entitled A RESPONSE SCORING SYSTEM FOR VERBAL BEHAVIOR WITHIN A BEHAVIORAL STREAM USING HANDHELD COMMUNICATING DEVICES WITH A REMOTE CENTRAL PROCESSING SYSTEM; and U.S. Provisional Application Ser. No. 60/885,583 filed on Jan. 18, 2007 entitled A RESPONSE SCORING SYSTEM FOR VERBAL BEHAVIOR WITHIN A BEHAVIORAL STREAM USING HANDHELD COMMUNICATING DEVICES WITH A REMOTE CENTRAL PROCESSING SYSTEM, the entire contents of which applications are hereby incorporated by reference herein.

BACKGROUND OF THE INVENTION

The present invention relates to Autistic individuals or special needs persons who have difficulty communicating with children and adults and, more particularly, to a system, devices and methods that are suited for monitoring and improving the training and social and eye contact and communication skills of such individuals.

Children and adults often require special services such as Speech Therapy, ABA (Applied Behavior Analysis) Treatment, Occupational Therapy, and Physical Therapy. These services are labor intensive, data collection is demanding and documentation is overwhelming. Educational materials are either prepared from cut-outs of a magazine/workbook or available through costly educational suppliers that do not integrate the educational material with a student's/patient's educational program. Local schools and communities spend valuable resources on repetitive and low level educational goals. Trained professionals burn out quickly. More time is spent on administrative chores than on training and advancing the skills of the professionals in their field.

Currently there is no central database of information available on the data collected during the behavioral treatment process, and inadequate tools, for example, standardized tools to use to easily gather and enter information about patients. Information about treatment and care is paper based and gathered ad hoc and at best, effective treatments are siloed or isolated within a school or clinic.
Learning Theories The principles of 'Behavior' have been identified by men like B. F. Skinner, F. Keller and W. N. Schoenfeld. More recently J. Michaels, J. W. Partington and M. L. Sundberg and D. Greer have elaborated and extended the categories of verbal and social behavior by identifying specific behavioral repertoires, functions and typologies that comply with the science and analysis of verbal, developmental and social behavior.

The prior art identifies various functional categories of verbal behavior, academic and social skills, and developmental stages. Assessments of verbal and social behaviors are done on a one-on-one encounter with the therapist or within a group setting. The therapist evaluates and identifies correct, incorrect, appropriate and inappropriate verbal, social and developmental behaviors within this setting. Sometimes timers and clickers are used to count and time the behaviors and responses that occur. The events are recorded in a manual fashion, i.e., a clip board and a pencil and based upon an isolated event.

The prior art identifies various systems for recording behavioral events that have occurred. The behavioral events are correlated with behavioral categories and are compared to the relative performance and fluency of other students (patients). Graphs are used to display the progress of the behavioral events. The data collection method is arduous, labor intensive and impacts the timeliness and reliability of the data, teaching and therapeutic methodologies.

When the service for the special need student/patient is provided in a home setting then issues like accountability, reliability and effectiveness of the behavioral stream data must be considered. Since the treatment is done in a home, professional supervision of the services being provided is unavailable. No one is able to view and suggest whether the intervention is proper, necessary or complete. Even the ability to verify that services were provided appropriately at the assigned location by the authorized person for the full amount of time requires additional personnel.

In addition, there are no standardized tools that are being used by professionals to help these individuals. Information concerning the type of tests and observations that have been made about individuals and about their progress is either not properly maintained or maintained in ad hoc fashions by professionals. Furthermore, the prior art has not provided a tool that might be utilized to improve the social skills, whether communications or eye contact skills, of the mentioned individuals.

SUMMARY OF THE INVENTION

Accordingly, it is a general object of the present invention to provide a system and method suited for defining these individuals' long-term behavioral, academic or social goal treatments in an organized, hierarchical relationship of skills and to create a database against which the level and progress of a particular individual can be measured.

It is a further object of the present invention to provide various tools which can be utilized by professionals in a standardized fashion to both collect information on the testing and other data pertaining to particular individuals and to provide other tools that help improve the social communication skills of these individuals, for example, by improving their eye contact skills in communicating with other individuals.

The present disclosure can be viewed as comprising two main systems referred to by the terms "TeachMe" and "WatchMe". The TeachMe system relates to that aspect of the present disclosure which concerns a system and method and applicable hardware that are designed to aid the collection of information about the training and testing of these individuals and the storage of related information, including background information, in a master, centralized database which is intended to grow over time to provide a standardized and centralized data available to all professionals against which the progress of individuals can be gauged and to which such progress can be compared and evaluated.

The WatchMe system relates to a specialized tool that is utilized in accordance with the concept of the present disclosure to improve the communication skills of the involved individuals by training them to gaze at or direct their eyes at the persons with whom they are communicating.

Other features and advantages of the present invention will become apparent from the following description of the invention which refers to the accompanying drawings.

BRIEF DESCRIPTION OF THE DRAWING

FIGS. 4a-4e are screen shots of the handheld device of FIG. 4.

FIG. 13 is a diagram of a biometric recorder.

DESCRIPTION OF THE PREFERRED EMBODIMENTS

The TeachMe System

The present invention (FIG. 1) allows the defining of a student's/patient's long-term behavioral, academic or social goals treatment plan in a hierarchical relationship of skills in treatment plans. It captures behavioral events within a 'behavioral stream' in real time and stores the 'behavioral stream' in a centralized database that can be accessed anywhere and at anytime using the Internet. Procedures and materials used during the treatment are identified. Data is stored in a central repository and can be displayed on the therapist's handheld device.

Figure 1:
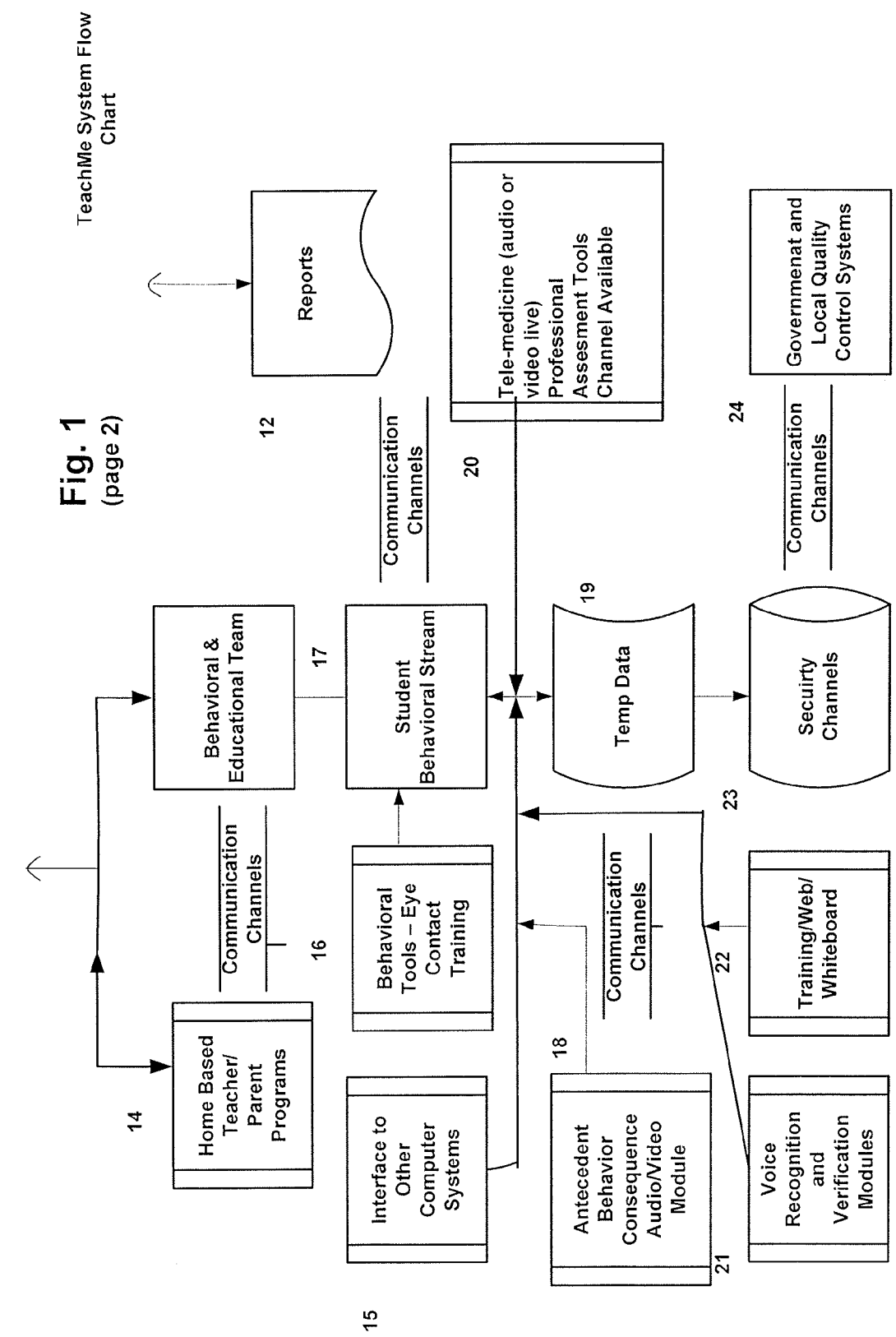
FIG. 1 is a TeachMe system flowchart.

FIG. 1 is a high level overview of the major components of the TeachMe system flow. With reference to FIG. 1, Block 1, Block 2, and Block 3 validates both the users and the devices used to communicate with the TeachMe system. The system checks whether there is an appropriate user and appropriate devices trying to access TeachMe. Block 4 checks and verifies that individuals and devices are providing services from the appropriate places using GPS technology and fuzzy logic.

Block 5 verifies the hardware and educational programs are up and running and available for use by the professionals providing services. In Block 6, the various curriculums are made available to individual professionals like Applied Behavior Analysts, Speech Pathologists, Occupational Therapists, and Physical Therapists. Each therapist in Block 8 customizes and updates the treatments and work plans for each patient or student. Block 7 is used to remotely synchronize the backend repository of the curriculum and treatment programs with the hand held device. The hand held device is used to collect and manage the treatments being applied to the student or patient either at a remote site or in a local school or clinic.

Block 9, Block 10, Block 11 and Block 12 implement appropriate security and control procedures like HIPPA, Health Insurance Portability and Accountability Act procedures and systems and monitors handheld devices that are synchronizing data collected during the treatment of students or when parents and professionals are accessing and viewing the data collected.

Block 13 is used to manage the administrative information about students, parents and professionals using the systems. The administrative staff updates information like, contact information, groups and policies, assigns permissions to individuals, student attendance and transportation information.

Block 14 checks whether the treatment and curriculum is being provided at a remote sight or a local school or clinic and will call Block 4 to verify that the appropriate person and device is being used to access the system. If the remote device and individual is approved then the behavioral team can begin to monitor whether the treatment being applied is adequate, appropriate and complete.

Block 15 is used to interface with other computer systems that may have educational and administrative programs which are used in the assistance of the treatment of the student and collects the data from those systems and sends to the current system.

Block 16 is used to transmit data from behavioral tools like specialized eye glasses that teach social eye contact behavior and transmit it to the current system.

Block 18 is used to monitor a student's behavioral stream and capture it using audio and video equipment.

Block 20 allows for video conferencing or the access of data by doctors, nurse or physician assistants to track any medical treatment that is being provided and impacting the behavioral treatment of a student. Block 20 will be also used in assisting in the delivery of the treatment as well.

Block 21 is used to allow the use of voice recognition to capture the spoken language used to communicate with the handheld device while capturing data during the treatment process.

Block 22 is used to train professionals and parents in the delivery of care using standard internet web systems like white boards and video training films.

Block 19, Block 23 and Block 24 are used by auditors to audit the educational and administrative programs used by the professionals and local schools and make certain it is in compliance with local state or federal regulations. It collects data from students' work plans and the various databases so that local and governmental auditors can verify that the school and professionals are in compliance.

Data collected on the handheld device during a session with a patient/student is transmitted to the host TeachMe application database. The data is used to allow the teacher and the rest of the behavioral, professional and medical teams to customize educational, behavioral and medical plans and goals for the student/patient. The data can be further analyzed as a repository of behavioral assessment and treatment plans that provides an understanding of which treatments are overall more effective than others The host TeachMe application contains browser screens for the teacher to enter information into educational plans. The browser screens can be used to monitor academic repertoires, activity schedules, social skills, verbal skills, stereotype behavior and the frequency of the presentation of material as well as the frequency and duration of treatment procedures. The screens can also be used to enter the fluency of a child's behavioral repertoires, criteria for success, and assessment tools and probes for stimulus generalization.

Figure 2:
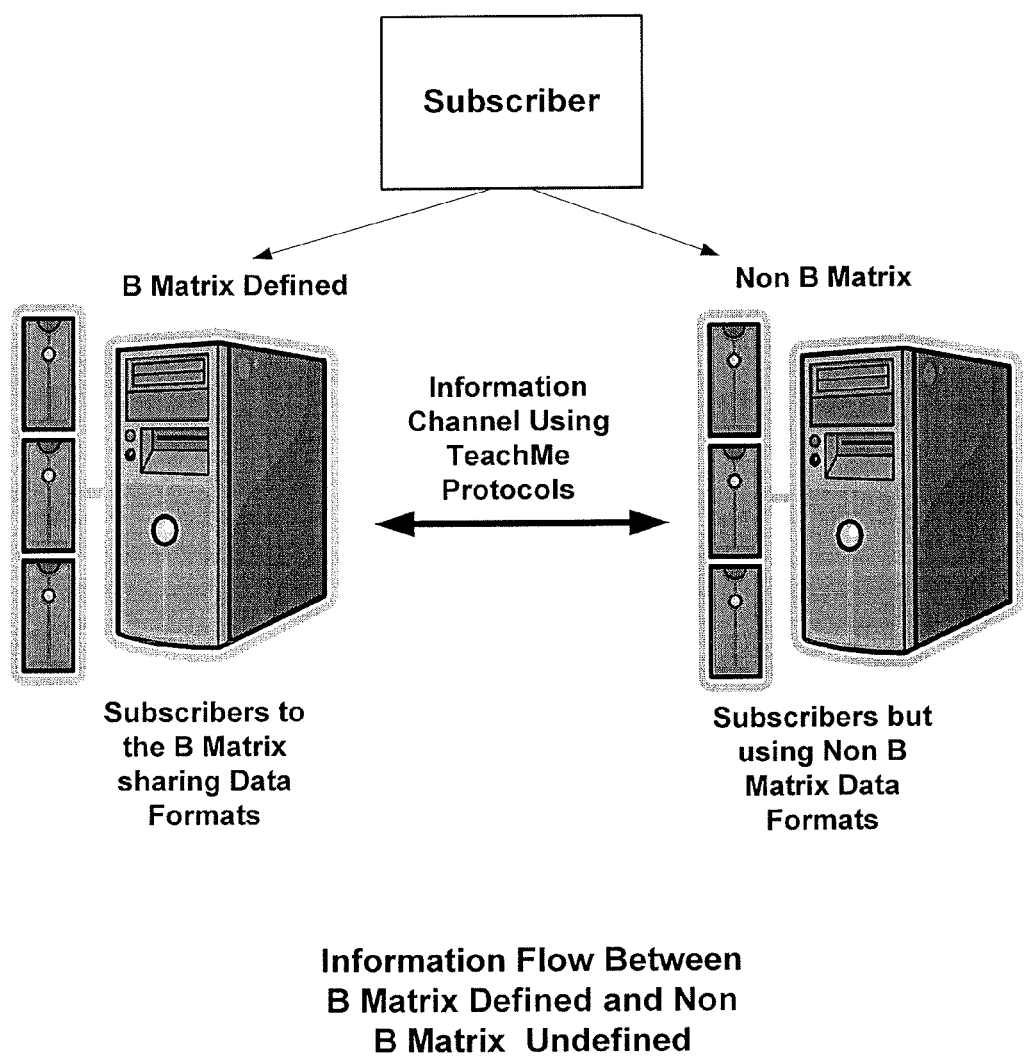
FIG. 2 is a diagram that indicates that a database can have a systemized and predefined arrangement of information and the arrangement of information can be contrasted to personally developed, non-centralized information.

The treatment data elements are organized in a behavioral and character matrix called the 'B-Matrix' (FIG. 2). The B-Matrix contains rules, storage and structures that monitor and track the efficacy of treatments applied in the acquisition of skills and monitoring of behaviors such as, biting, hitting and other similar traits. The B-Matrix will contain the standards that emerge from the behavioral and character treatments. The B-Matrix creates a global depository that can be used by schools, agencies, universities, parents and many others to draw valuable data for the use in treatment, analysis of data, performance analytics and for a myriad of other applications in the areas.

The B-Matrix is designed to be an open standard available to be published. TeachMe references "B-Matrix defined" and "non-B Matrix". The B-Matrix defined property can refer to, among other things, an activity, skill, social event, appropriate and inappropriate behaviors within the behavioral stream. These are defined values that are part of the TeachMe system. They are entered into the B-Matrix dynamically by the users of the system. When an organization uses the TeachMe system, it has a choice of either using the B-Matrix defined values or to create its own values, referred to as "non-B Matrix. This is not an either-or choice. An organization can mix B Matrix defined and non-B-Matrix values wherever it chooses and where it is allowed. An organization, however, can never modify or delete a B matrix defined value or modify its meaning. An organization can switch back and forth between its proprietary definitions/formatting and those belonging to the B-Matrix. The system interfaces can display data according to the B-Matrix standards or according to the organization's layout.

As the TeachMe databases increase in size, the B-Matrix grows into a mature foundation that can be used by everyone in a unified way. Organizations will have the ability to view their data formatted according to the B-Matrix standard. Reports can be generated to indicate where non-conformance exists, so that the organization can modify their format to conform to the B Matrix format, should they choose If an organization reformats its data to the B-Matrix format, it is possible to identify that organization as being "in conformance". This could is useful when exporting/importing an organization's data to and from other organizations that might have to deal with the organization. In effect, TeachMe has a "B-Matrix Certified" certification, which is granted to any organization that conforms to the 'B-Matrix' format. This could help parents and clients seek organizations that conform to the B-Matrix standards. Since the evaluation of an organization's conformance is done programmatically and under very strict guidelines, it is possible to have instant conformance validation done at any point in time. Since no human intervention is required, there is no bias involved; either an organization conforms or it does not. The organizations using the TeachMe system can participate, if desired, in the layout of the B-Matrix. Participants of the TeachMe system can contribute layouts to the B-Matrix.

The B-Matrix is designed to also be culture-independent and locality-independent. It is reasonable to assume that given a large enough database covering thousands of patients and therapists across the globe; it is possible to identify common attributes and methods of treatment that can be universally agreed upon and used. Anything that is culture-dependent can still be included in the B-Matrix but it is marked in such a way to identify it as being culture-specific.

System Overview

It is the goal of TeachMe to provide families, professionals and the students/patients themselves with the technology to access a repository of behavioral treatment programs that can be implemented, recorded and evaluated.

TeachMe uses various standard wireless remote or cabled connections protocols to communicate over the Internet, Intranet or LAN Servers to transmit the results of behavioral treatment program and obtain changes in the treatment program.

Teachers, applied behavior analysts, speech pathologists, occupational therapists and physical therapists use the assessment tools and the behavioral treatment programs on the host web server to prepare daily activities for their students/patients.

The TeachMe technology captures the student's mastering of the treatment programs designed for him. It compares the treatment programs with functional and standardized assessment tools that could be used to periodically evaluate the goals set for a student.

Figure 3:
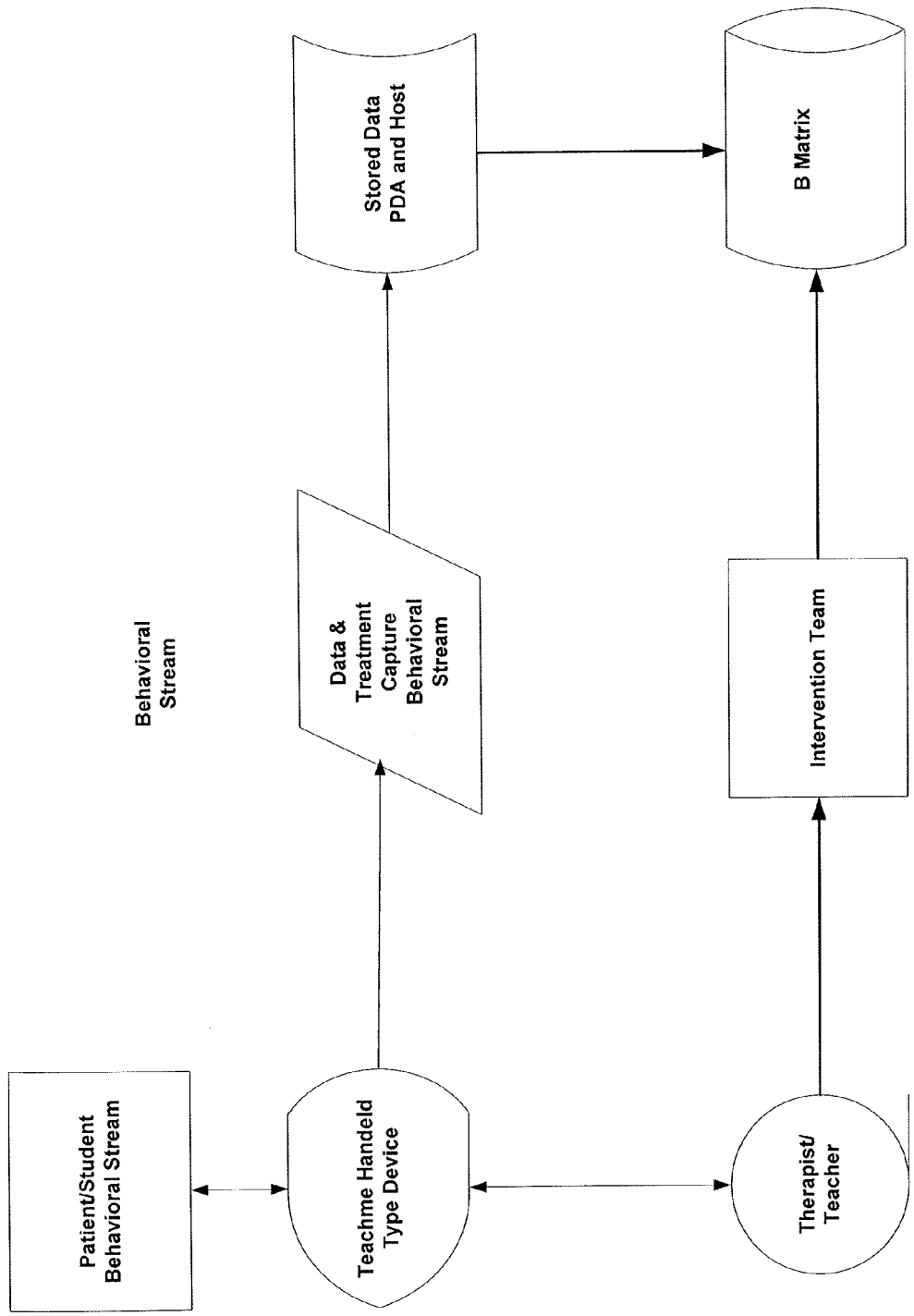
FIG. 3 is a diagram of a behavioral stream.

As the behavioral treatment is applied, the students' behavioral streams' (FIG. 3) data becomes available to the organization's authorized users. This allows parents, professionals, schools, or agencies, even when not within proximity of a student/patient to respond with the appropriate interventions and treatments and to modify existing treatment plans if necessary. Since this data is available to treatment professionals, an organization can at any time and any place produce a more effective, reliable and accurate treatment process. It can monitor the student's mastery and fluency of skills and note any stereotypic or inappropriate behaviors. It can evaluate care being provided and compare the planned with the actual service.

The educational and behavioral treatment programs are created either on the handheld device or remote host server environments. The handheld device contains information about goals and defined activities and their attributes like trial definition, probe definition, number of trials, success criteria, protocols for continuing or stopping the treatment, timing and event values of the treatment process, single or chained activity treatment, and schedules of treatment. The handheld device records verbal behavior and compares the quality and quantity of the verbal repertoire of items like mands, tacts and intraverbal behaviors. It notes the tone, volume, duration, strength, frequency and rate of the verbal behavior. TeachMe provides reports on the quantitative and qualitative data.

The therapist taps, clicks or emits voice commands associated with a specific behavioral response to record the accuracy of a response or description of a behavior. As the therapist uses TeachMe to monitor the treatment programs, TeachMe date and time stamps each event that occurs within the behavioral stream, it records the number of correct or incorrect behavioral responses and the level of prompt, it calculates response time and reaction time. It collects interval and/or duration recordings, independent and self initiated responses, rate, latency and fluency of responses. The handheld is able to collect data from individual one-on-one sessions as well as group sessions.

Application

Figure 4:
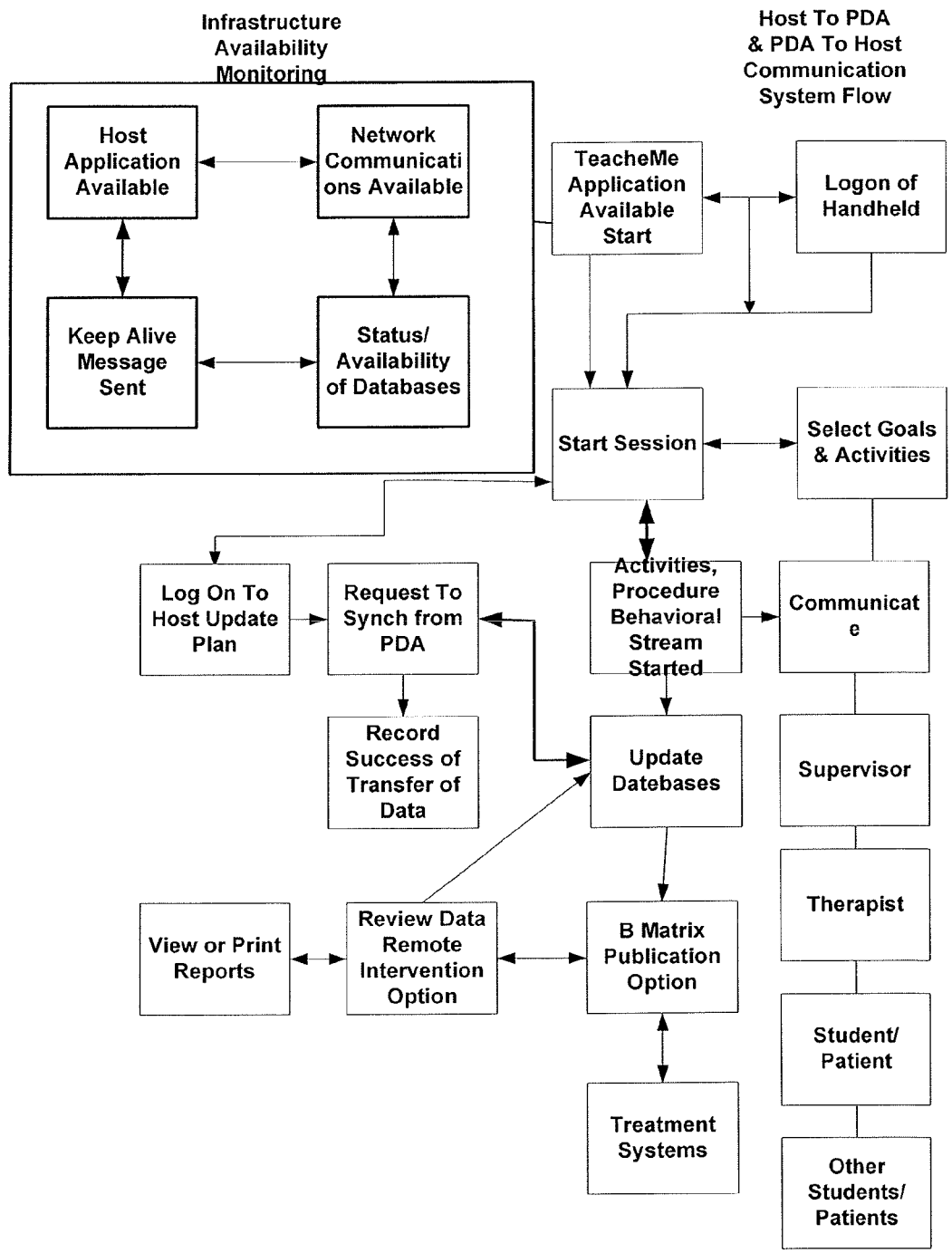
FIG. 4 is a flowchart showing a general infrastructure of the TeachMe handheld device of the present invention.
Figure 4A:
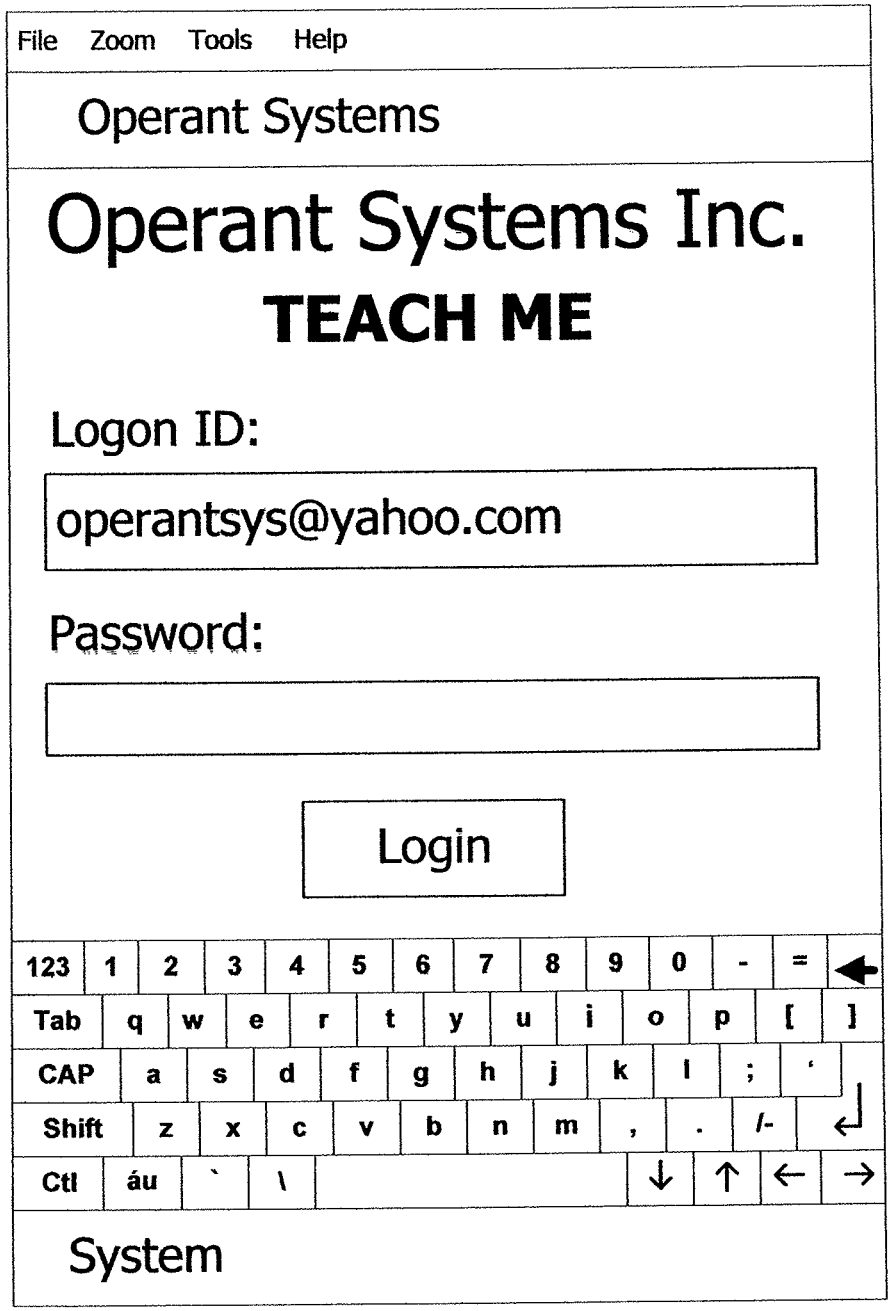
Figure 4B:
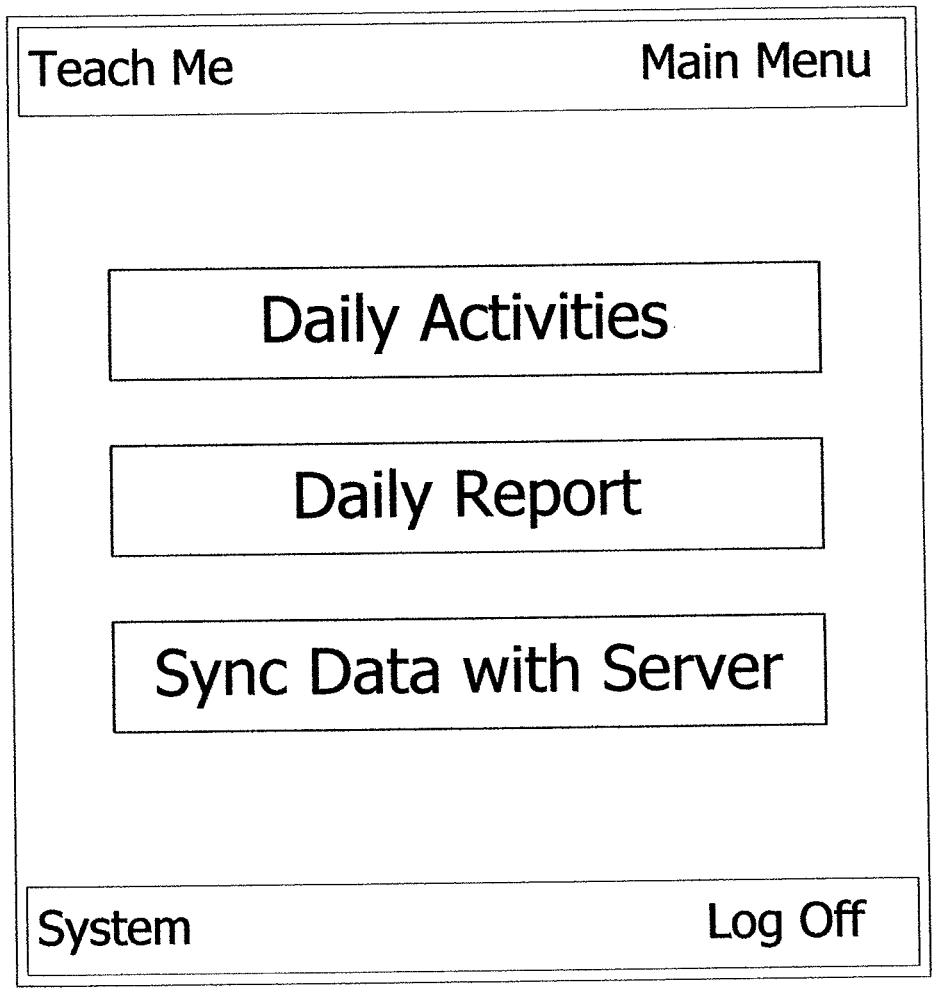
Figure 4C:
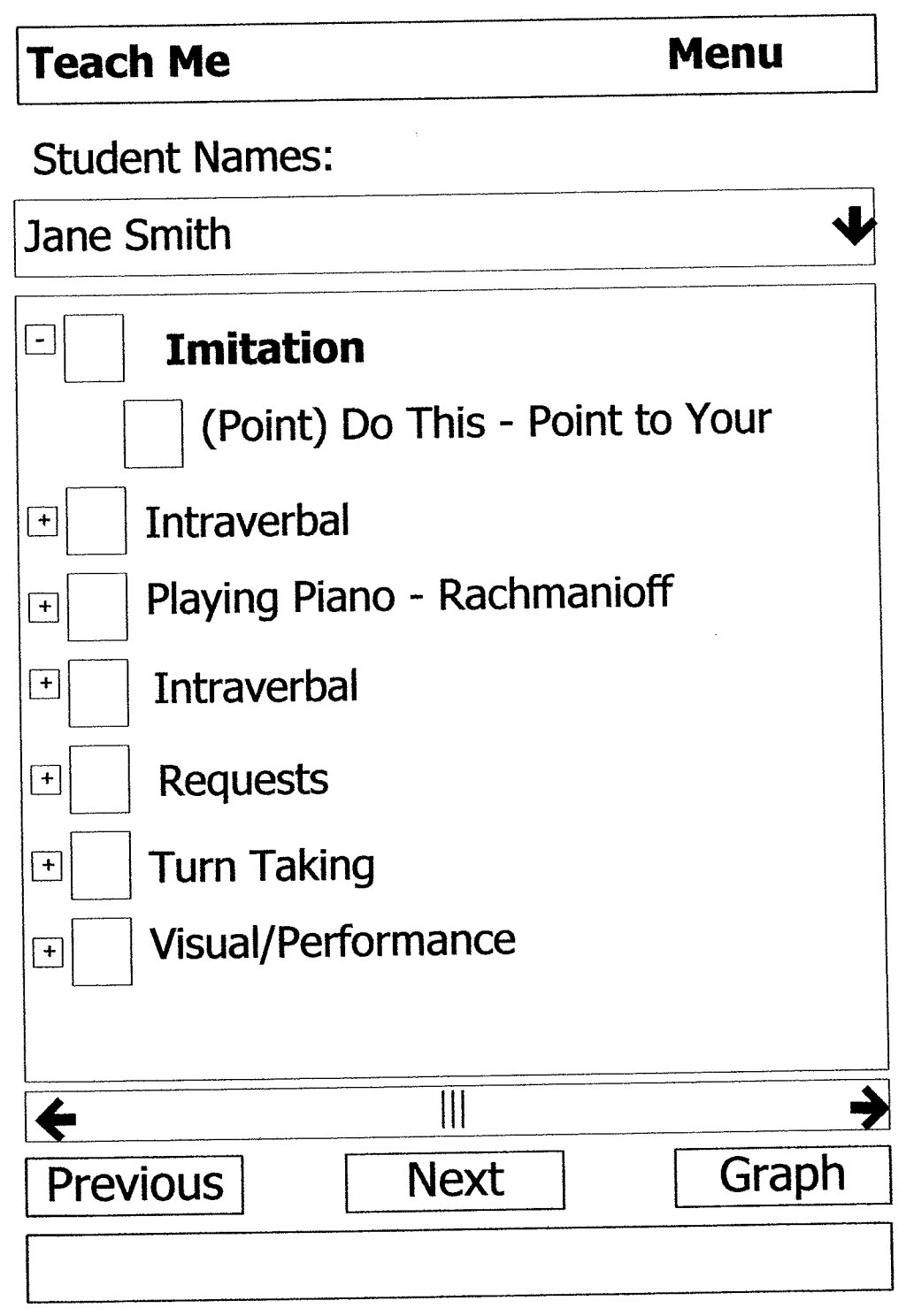
Figure 4D:
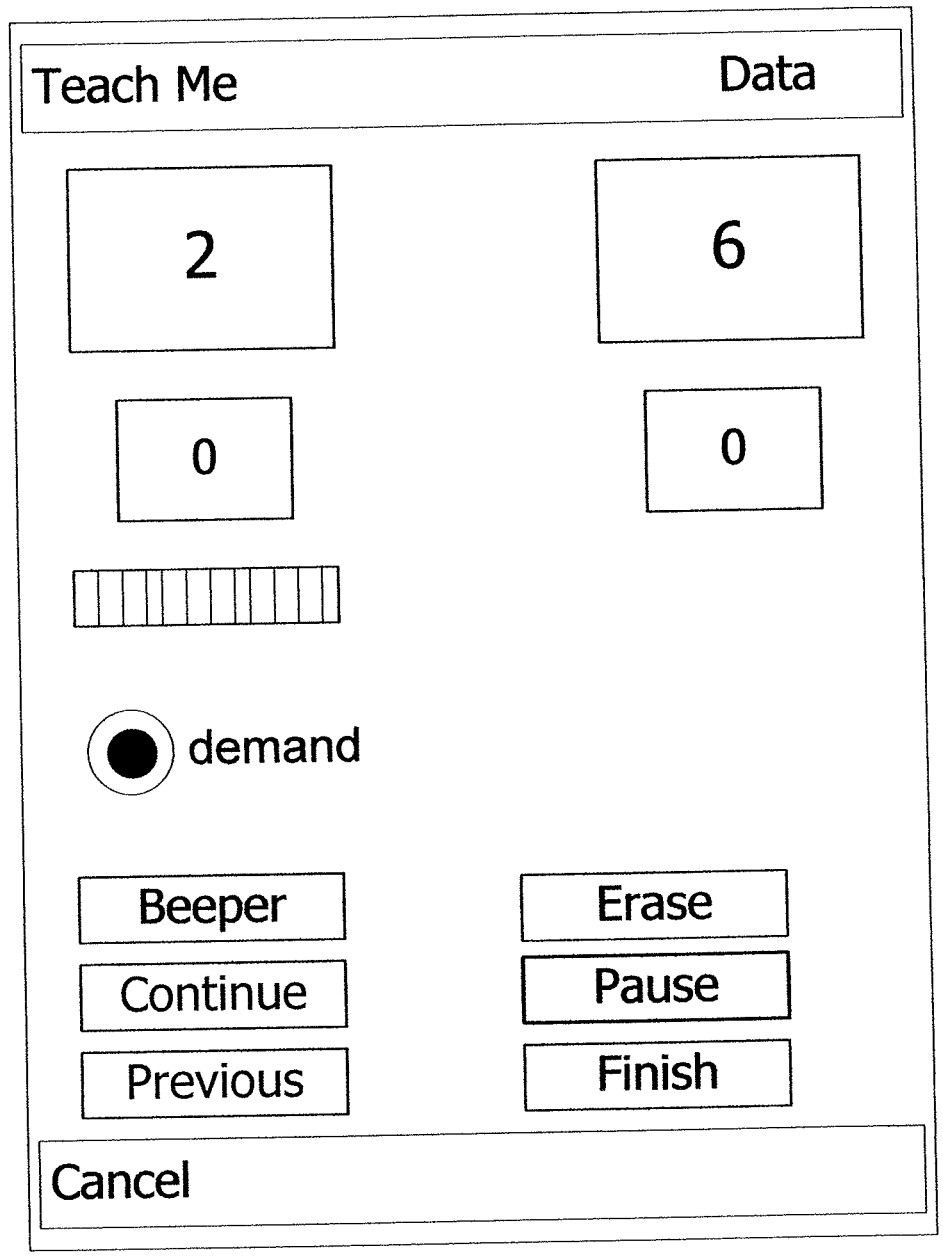

TeachMe handheld device, of which its block diagram is shown in FIG. 4, is turned on and the user validation module is run. User validation can be done through voice verification or recognition, a biometric system like eye ball identification, voice prints or other common biometric identification systems or through standard stylus or keyboard input. TeachMe has the capability to compares log information with the validation information. TeachMe requests a valid ID and password to access the TeachMe application. It then identifies and validates the user of the handheld device. A teacher could start the session by selecting the student/patient treatment programs to teach or observe, e.g., to teach manding, speech vocalization, fine motor coordination, imitation etc., or a student/patient could select from a schedule of activities what the student/patient would like to participate in. Screen shot examples of the TeachMe handheld device are shown in FIGS. 4a, 4b, 4c, 4d, and 4e.

The TeachMe handheld logs itself in and validates itself as a secure and approved device (FIG. 13). The handheld can become the device of a master teacher, teacher, or student/patient device. As a master teacher device, the handheld primarily communicates with other teacher devices and student/patient devices. The master teacher detects and monitors whether the behavioral stream being observed is occurring locally within a school like environment or within a home based environment. The master teacher TeachMe device monitors, observes and collects data from other teacher devices. The master teacher device monitors the accuracy and reliability of the scores collected by the teacher handheld device. As a teacher device, the handheld primarily communicates with students/patients devices, or other teacher handheld devices. TeachMe students/patients devices can notify a teacher TeachMe device that is involved in a behavioral activity that it is ready to transmit the results of his or her behavioral activity.

The TeachMe handheld sends results of the lessons to the host site and receives data from the host site through communications protocols. If the education is occurring within a home based environment the communication to the TeachMe host application occurs through wireless, dial telephone or a cable connection to the Intra/Internet or LAN. TeachMe captures the educational activities and displays the results on the teacher hand held device as well as the master teacher devices. This allows the teacher and master teacher or any other professional to respond to issues that may be evolving from the educational program.

The teacher, student/patient can select the defined and established teaching or assessment modules for that day or allow a student/patient to proceed to select the sequence of their own activities from a schedule or a given set of options. The teacher, either by himself or conjunction with other trained professionals, defines criteria for completion, mastery and maintenance. The criteria are either intra session, like if a student/patient emits ten consecutive responses in a row, or inter session, like a student/patient emits ninety percent correct on the educational program 3 days in a row for 2 ten day periods. If the intra or inter session criteria are completed the student/patient can go on to his/her next learning module.

The data collection process not only occurs for single individual events but also for multiple concurrent events for single child or multiple children. In the 'free operant environment', TeachMe will be able to count and time the behavioral stream of single or multiple children.

Once the behavioral goals for the day are selected, a number of scoring and recording modalities are available, including 'free operant' observations of various students' behaviors, discrete trial training of correct and incorrect responses to trials, monitoring of appropriate/inappropriate responses. A PC Tablet and handheld can be used to spawn auditory or visual discrimination training programs, academic literacy math and reading programs, activity schedule training, handwriting and tracing performance.

Figure 5:
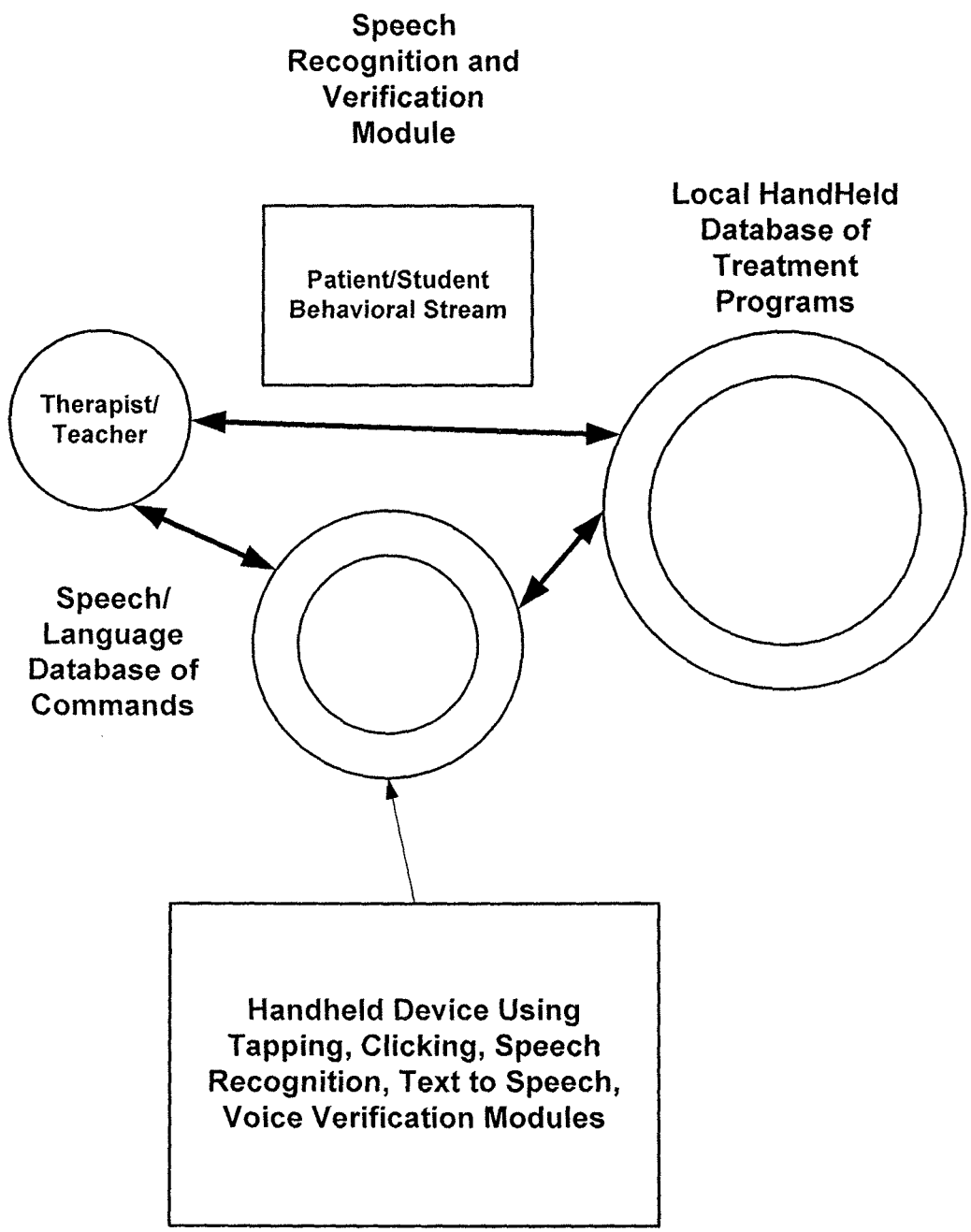
FIG. 5 is a diagram of a speech recognition and verification module.

Each time a verbal, social event, or any event occurs, the teacher marks the event by tapping appropriately on the handheld device, clicking a rolling ball on a selected item, or providing voice commands. The voice commands can be as simple as, 'Good Job', 'Next', 'Previous', 'Graph', 'Print', or more involved statements, 'Find Next Lesson Dealing with 'Imitation Skills'. The teacher or therapist communicates verbal commands with the handheld device (FIG. 5) either using an attached or wireless like microphone or a Bluetooth type headphone to issue the commands to TeachMe. TeachMe provides a feedback mechanism which demonstrates that the proper command was executed. The feedback could be in the form of tones, spoken words contained either in the speech recognition, speech pattern matching database or in the text to speech translation module. As the teacher taps, clicks, or emits commands to the handheld device an event recorder can be used to record the event. The number of 'taps' or 'clicks' that indicate the teacher or therapists responses is designed to keep the navigational time at a minimal. The goal of the system is to provide direct access to selected educational events and either count or time those behavioral events by using a single tap, click or emitted voice command.

Figure 6:
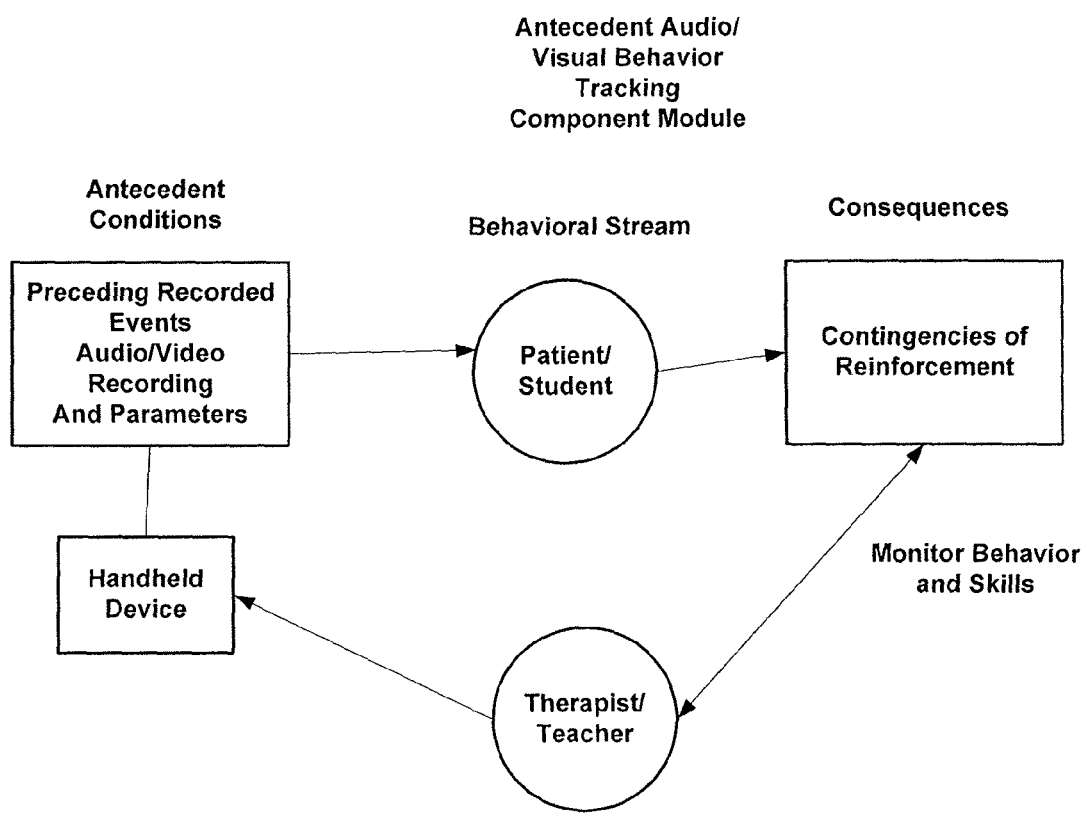
FIG. 6 is a diagram which depicts taking periodic audio and video snapshots of the behavioral stream being monitored.
Figure 12:
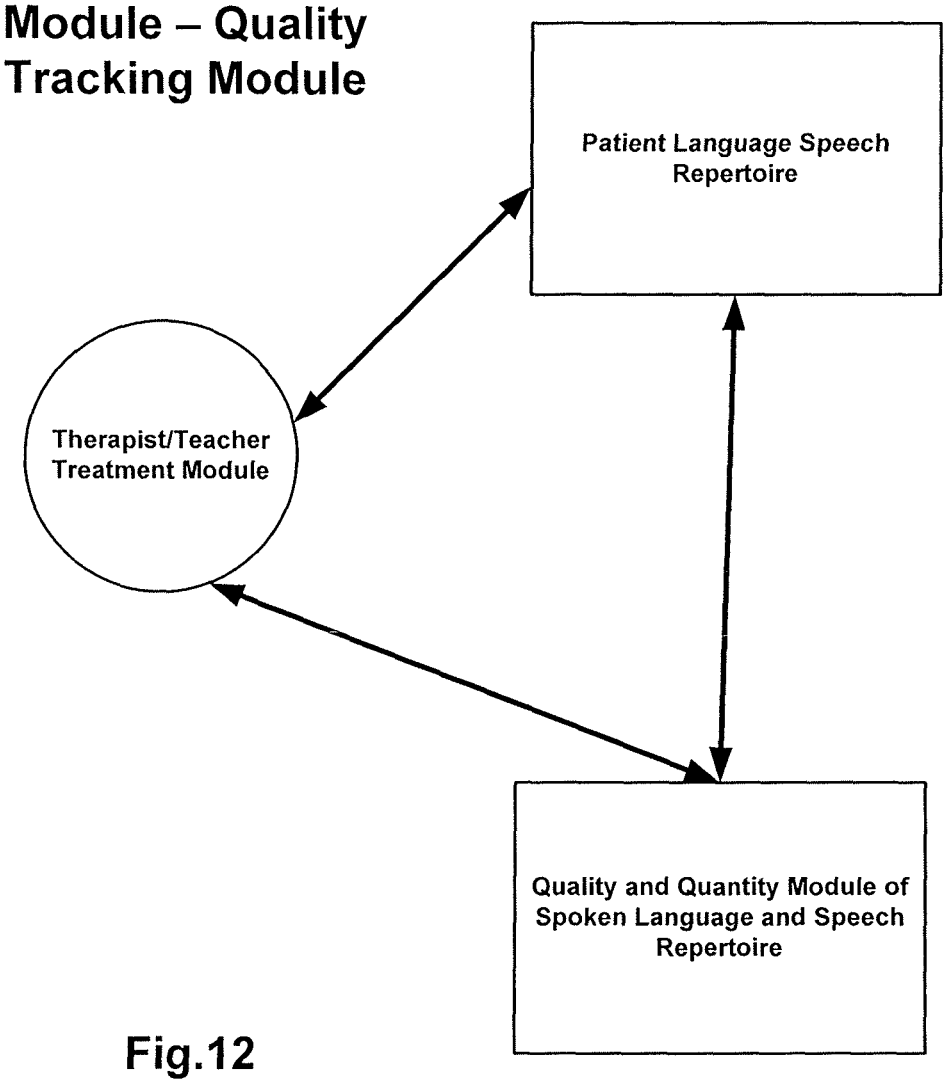
FIG. 12 is a diagram of a speech quality tracking module.

TeachMe makes available audio recording buttons to record behaviors or specific activities throughout the day. The teacher's handheld device also communicates with an audio/video device to start recording an event within a behavioral stream. This synchronizes the teacher recorded event with the students'/patients' verbal behavioral event. The audio/video recorded information can be later used for further analysis, reporting or archival purposes. The audio recording module (FIG. 6) also samples sounds in the teaching environment, and either continuously records the sounds in the environment or allows the teacher to modify the recorded sound by using an overwrite parameter defined in the module. TeachMe can also activate video recording system to record, archive and study the behavioral events of the day. The audio recorded data can later be retrieved for review and study of the educational process. The audio recorded information is analyzed by a voice recognition and verification module that can be used for transcription and authentication. There is also a module (FIG. 12) in TeachMe which compares the quality and quantity of the verbal repertoire of items like mands, tacts and intraverbal behaviors. It notes the tone, volume, duration, strength, frequency and rate of the verbal behavior. TeachMe provides reports on the quantitative and qualitative data.

Figure 7:
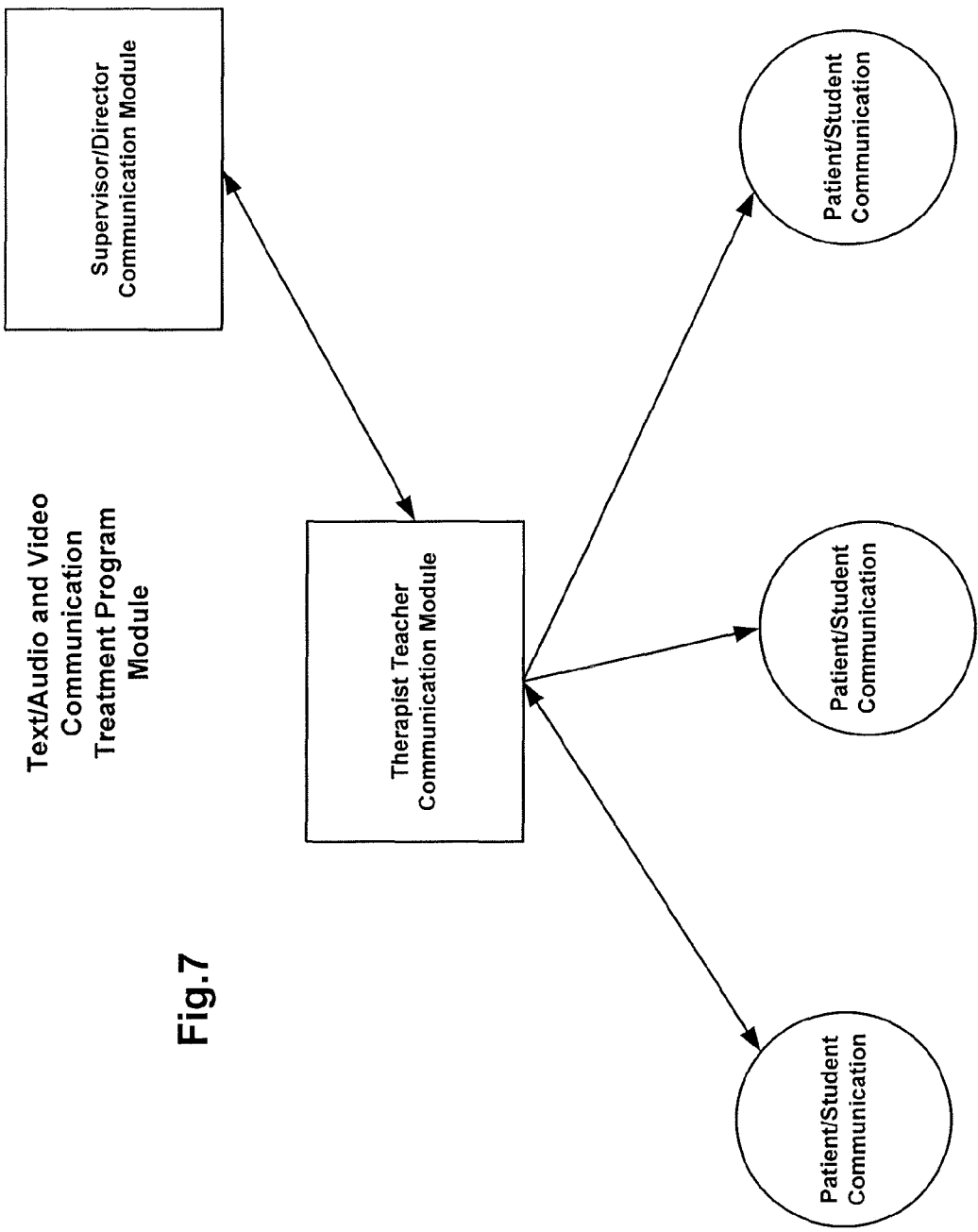
FIG. 7 is a layout of a text and audio/video communication module.

The handheld text messaging module allows students/patients to send messages to other students/patients, teachers, supervisors or others involved in the treatment programs. TeachMe not only monitors expressive and receptive verbal language events but also monitors written communication events. The text messaging module (FIG. 7) looks at the number of text messages, the length of a text message, the complexity of ideas presented in the text message, the grammatical structure of the text message and the semantics of the text message. By analyzing each of these components TeachMe can report on the level of the student's/patient's written language.

The professionals can also communicate (FIG. 7) amongst themselves using the handheld audio channel. They could review the status of the treatment being provided with each other or communicate directly to the child.

TeachMe's correlates the reported data with the various functional or standardized assessment tools and therefore develops more accurate and reliable teaching activities. For example, if a student's/patient's intraverbal behavioral results score indicates the need to enhance their intraverbal social repertoire then appropriate daily skills can be targeted and future teaching strategies can be made available. The daily monitored activities are correlated to the functional and standardized scores and results.

Interfacing to Other Technologies or Lessons

Figure 8:
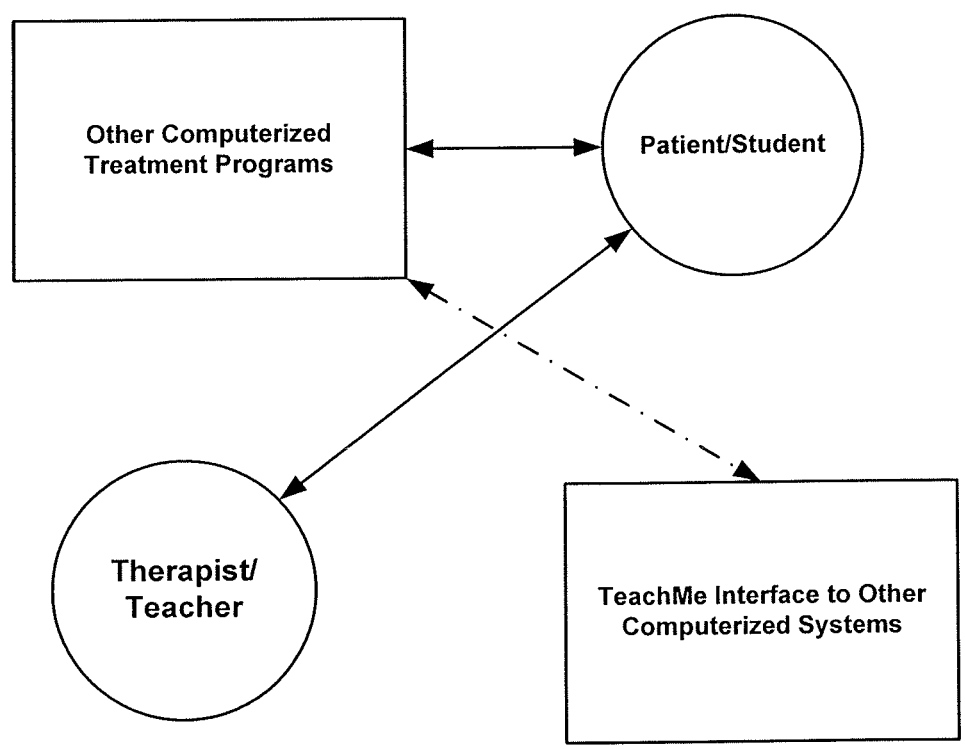
FIG. 8 is a further diagram of a behavioral stream which interfaces to other educational or instructional systems.

TeachMe interfaces and can spawn instructional and treatment activities (FIG. 8) that are available on a computer system. For example, if a student/patient is participating in a computer assisted system reading program, the data collected between the interaction of the reading like number of correct response, rate of the responses, percent correct responses and the student/patient will be collected and displayed on teacher handheld device. The student/patient handheld also provides educational sessions like matching to sample programs and auditory discrimination. It can record and transmit the behavioral events to the teacher's handheld. This will allow the teacher and master teacher or any other professional to respond to issues that arise during an educational program.

If no network connections are available to the host server TeachMe allows the creation of the daily activities, their attributes and goals to be entered on the PDA. This information will later be sent to the host server on the Internet, Intranet or LAN host.

Figure 9:
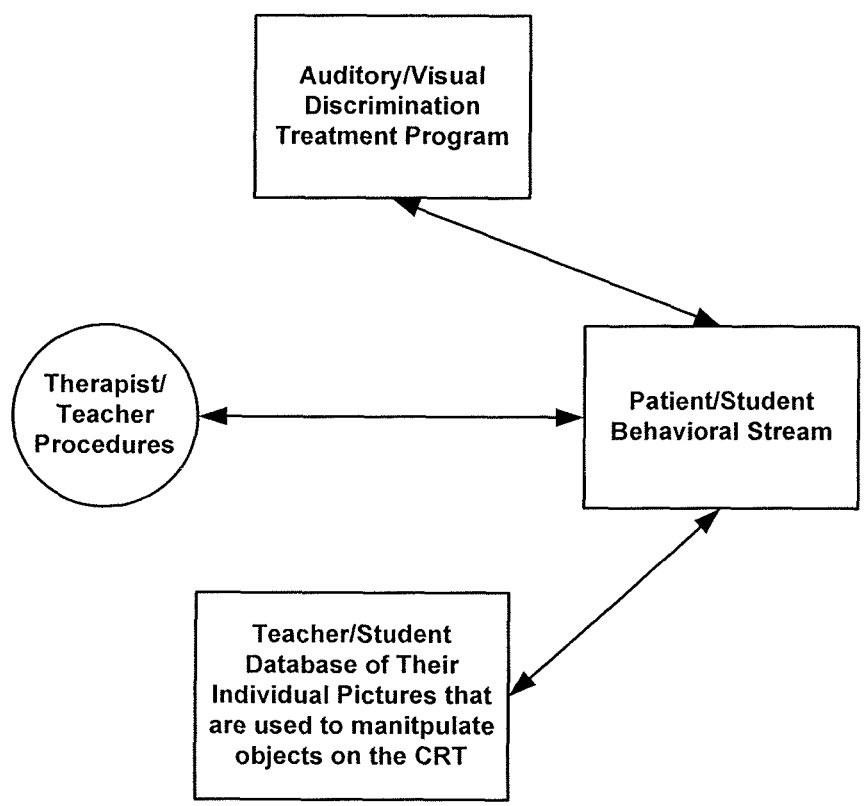
FIG. 9 is a diagram of an auditory and visual discrimination module.

The auditory and visual discrimination modules (FIG. 9) use interactive teacher and student captured self images to manipulate the choice options available in the discrimination teaching module. When a random set of pictures and/or sounds are presented by a picture of the teacher the student then uses the student picture through touch screen and other input methods and then selects his picture to select the appropriate choice. This provides 'the touch and feel' as if the student were interacting with their 'real' teacher. This approach is used to strengthen a student's understanding of his 'self' image'. So a discrimination program can display the following: the teacher's picture which says 'Here are two sounds', two pictures making a sound of a bugle and a whistle. The next picture comes up and the makes the sound of the bugle. The student then takes his picture and selects the appropriate matching sound. The student and teacher picture are contained in the host database.

TeachMe provides step-by-step tutorials to deal with challenging after school behaviors, either through text instructions, live video connections, or video clips available on the handheld device to train parents and paraprofessionals in specific deficit skills and techniques. Webex conferences and white boards are used for teacher and parent training.

Life skills modules like tying shoes, brushing teeth, eating with a utensil, folding clothes will be available to parents so they can better manage and handle their child's 'life skills' deficiencies.

TeachMe provides 'Telemedicine' services either through recorded or live communications services which provide professional guidance, testing and medical services.

Administrative & Security

The current system also interfaces with various governmental and regulatory systems and provides them with administrative information, e.g., student/patient attendance and the progress of a student/patient performance. The current system verifies that all educational services are provided for the specific student/patient within the designated timeframe, and within the predefined educational programs. TeachMe can also be used to evaluate future governmental required evaluations, like the Instructional Education Program (IEP) or an Independent Family Service Program (IFSP) for the slow or advancing students/patients. Professionals in the field can look at the data and determine what type of ABA treatment, Speech, Physical or Occupational therapies are needed. The frequency of needed resources can be driven by the instructional results.

To maintain the confidentiality of a person's records, security channels constantly monitor the TeachMe application modules for compliance with government regulations like HIPPA.

At appropriate times the Internet, Intranet, LAN host online system communicates with various governmental agencies or school systems to provide information like a student's/patient attendance, transportation information, site information, teacher session notes, team notes and parent comments on the skills and behaviors being treated.

Figure 10:
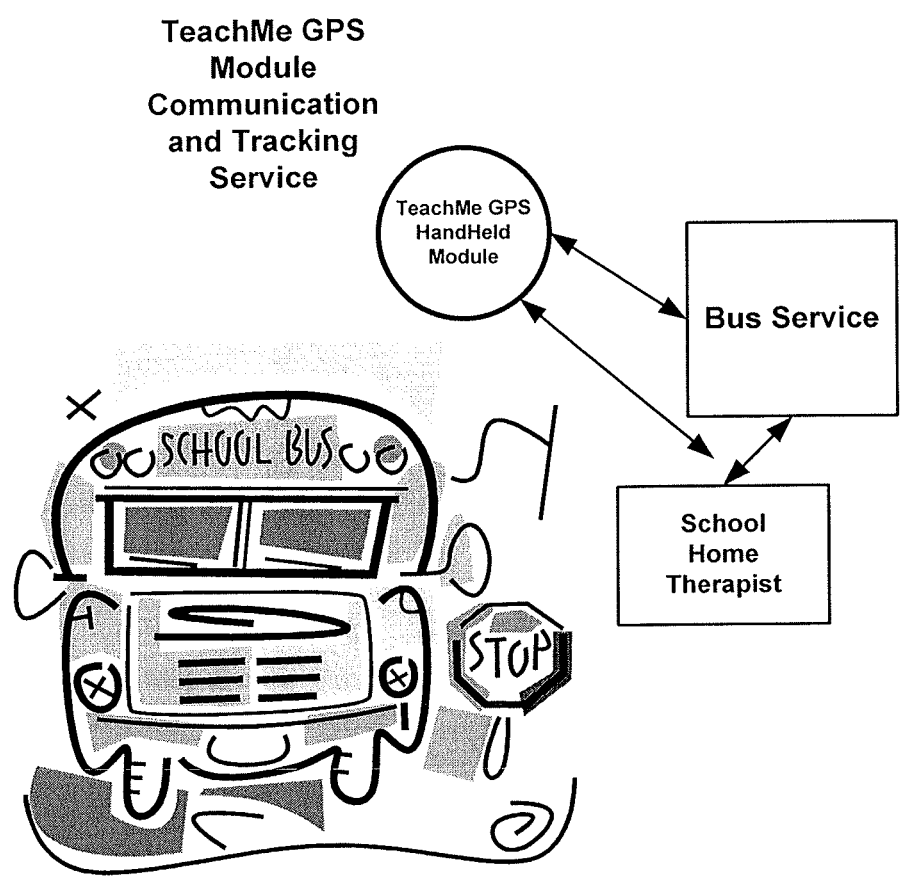
FIG. 10 is a diagram of a system which allows location of both trainer and trainee, using a GPS system.

The TeachMe's GPS Authorization and Verification module (FIG. 10) identifies the location of the service being provided, who is receiving the service and who is providing the service. A picture or video of the child can be taken during the treatment and either stored and forwarded to the host site for later verification or it can be compared in real time with the picture or video of the student/patient in the database. TeachMe can also verify who is providing the service through, signature comparisons, biometric devices like finger printing, the use of logon IDs and passwords, handwriting recognition or verification modules.

GPS

TeachMe also has a transportation module in (FIG. 10) to track transportation services of the student/patient to and from a school, or a home based program where the teacher or therapist travels to the student's (patient's) home. If the services are provided in a school or a center then transportation module will start the data collection process. Students/patients of special needs have defined times and limits when their treatment can occur. Professionals assigned to work with the students/patients are scheduled to provide services at specific times. The GPS feature monitors that teacher traveling to a home is in fact in the home and performing the treatment as scheduled. Treatment that is delayed effects the development, status and flow of the behavioral stream. Unusual circumstances can occur affecting the special needs of students/patients. The GPS is also useful in monitoring the public or private bus companies that have an obligation to bring students/patients with special needs on time. If transportation drivers are late or lax in their commitment, special services treatments are delayed or missed. Therefore, transportation companies providing commuting services for special needs students/patient will use the handheld TeachMe device with the GPS module which will allow schools and other concerned bodies to view the traffic location of the vehicles on the Internet, Intranet or LAN and allow the school to see the status of the vehicle in transit. Communication messages like email or text messages could be sent as to the status of the children and whether parents or guardians need to be available to pick up the child. If young children are being transported, then incidents like abuse, diaper soiling or wetting can be tracked. Transportation companies that frequently come late could be dismissed from contracting with the governing municipality or other contracting bodies.

Figure 11:
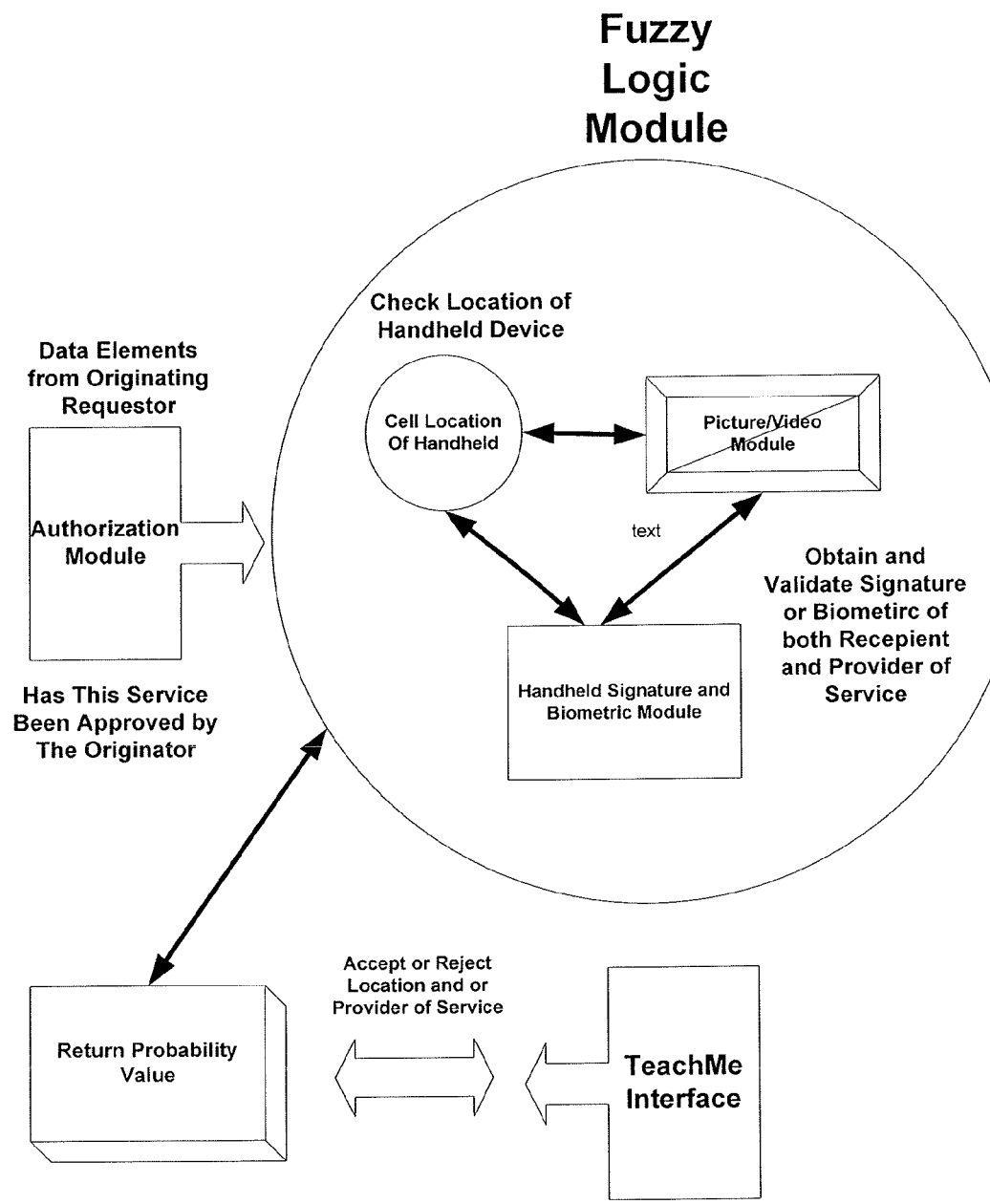
FIG. 11 is a diagram of a fuzzy logic module.

If a GPS type cell phone or similar handheld device is being used to manage the treatment process then the 'fuzzy logic' module (FIG. 11) is available. The module evaluates three identifying elements. These identifying elements are used in a 'fuzzy logic module' that comes back with a result which says there is a high and reasonable probability that the provider of the service is in fact the appropriate person at an acceptable location or not. The elements of the 'fuzzy logic' module can used with either independent or dependent elements.

If dependent factors are used in the fuzzy logic equation' the 'K factor' is evaluated in addition to the independent values. The K factor are the assumptions that must be evaluated in addition to the independent elements.

If independent elements are the components of the probabilistic statement then the 'fuzzy logic algorithm' assigns a probabilistic value to each element of the probability equation a percent value. The product of all the values is used to determine whether the event is either false or true. True or an acceptable value for the user of fuzzy logic equation, says the right person is at the right location. The 'False' indicator says that the either the wrong person is at the right location or the right person is at the wrong location because the probability value is less than an acceptable value.

The three elements of the current 'fuzzy logic' equation is the users active GPS device used to make a phone call to a designated number, a signature from either an approved authorizing individual or recipient and provider of a service and finally a video or picture of the recipient of the service or approved authorizing individual.

The GPS cell phone call information provides the date and time of the call and the geographical area of the call. The coordinates of the call and the date and time of the call are sent to the 'fuzzy logic module'. The 'fuzzy logic module' compares the coordinates of the cell call with coordinates of the location of the service or the recipient of the service and determines if the actual call is within the planned location. If there is a high level of probability that the geographic cell is in the same geographic location of the recipient of the service or approved location of the authorizer of the service then the first element of the 'fuzzy logic' equation is assigned a high probability value like 0.9 that the call is coming from an appropriate location. If the results comes back with a value that is 0.5 or less a message is sent to the TeachMe system not to proceed with the service.

If the value is 0.6 or higher from the cell call then the next element of the 'fuzzy logic' equation is analyzed. The next element of equation says 'get a signature' from the recipient of the service. Collect and store that information for analysis either in real time or using a store and forward procedure.

The signature is stored and forwarded or analyzed in real time. The signature is either compared with a signature in a database of valid signatures or is just collected to be viewed in a report that prints out signatures. If the signatures of the recipient of the service and the provider of the service is sent to the 'fuzzy logic' formula of 1.0. The product of the previous element of the fuzzy logic equation, i.e., the cell call phone and the compared signature is computed and the results are evaluated and determined if they are within a defined acceptable range. If the value is within an acceptable range the equation comes back and says it is highly likely that the right person is at the right location and a message is sent off to the TeachMe system that the provider of the service should proceed with providing a given service.

If the signature is not compared but rather stored and forwarded so that at some point an auditor can check can whether a signature is on file then another element of the 'fuzzy logic' equation is considered and evaluated. The user of the GPS device is asked to take a picture or video of the site which the service is being provided or authorization is occurring.

The GPS handheld device takes a picture or a video of the recipient receiving the service or the picture of the location of the office in which the authorization is occurring. The picture is date and time stamped and the watermark of the picture is captured. The 'fuzzy logic module' stores or forwards the picture for later analysis or analyses in real time whether the picture is authentic or a forgery. The results of the picture analysis can include a comparison of stored and valid pictures or videos with the current picture or video or no comparison of picture are made but rather the fuzzy logic module analyzes the watermark and date and time of the picture and determines whether the date and time and the watermark of the picture are consistent with the date and time of the service and authorization. The fuzzy logic statement is not necessarily providing certainty but rather a high degree of probability that the picture taken occurred at the right time and has a new watermark. The results of the probability of the picture analysis is sent back to the 'fuzzy logic' algorithm. If the value is 0.6 or higher than the 'fuzzy logic algorithm' computes the product of all three elements of the equation and provides a probability value that says whether to accept the call from the GPS device, indicating that the right person is at the right location or not. If the value is 0.8 or greater or some other value that is acceptable the 'fuzzy logic module sends a message to the TeachMe system to proceed with approving the service based on a phone call from a GPS cell phone or not.

On the administrative level TeachMe contains a module that supports the day to day administrative programs like a payroll/billing and general ledger module. The administrative module contains the mandated governmental IEP (Instructional Educational Program), or IFSP (Independent Family Service Plan), attendance and transportation information, teacher licensing, personal data and attendance information, and quality assurance data to meet governmental inspections. Periodically the administrative module interfaces with governmental reimbursement systems for payment of services.

The administrative module allows for more accurate billing. Overpayments are denied and underpayments are adjudicated. This reduces the costly external and internal audit services to more reliable and accurate report on a school's administrative costs.

The 'Telemedicine' module monitors and tracks medical and aberrant behavioral events and provides the appropriate medical support and treatment plan using either live audio or video communications or pre-recorded audio and video information. The 'Telemedicine module mines the data within the behavioral stream and provide to physicians, nurses, psychologists, physician assistants access to this information. In turn the 'Telemedicine' staff responds with the appropriate treatment plan. Where medication is required the parents and other professionals can be brought in a timely fashion to evaluate medical treatment. This will allow rural sites to also obtain effective treatments.

Training Module

The Training Module allows professionals to acquire online training through WEBEX, live video and audio conferences and interactive whiteboards between the hosts and professionals. This will allow the students/patients, teachers, paraprofessional and professionals treating the child to advance in their skills.

The training module also allows professionals, teachers and other practitioners with self-teaching video modules. A professional can view videos of past treatment effects and score the appropriate treatment needed. Scores are compared between the actual treatment paths with score obtained. The training module is used to better train professionals and enable them to conduct the appropriate research in their fields. It gives parents better insights on how to care for their children.

The WatchMe System and Device

In general, the socializing skills of the above-described individuals are poor or non-existent. There are, therefore, various behavioral training programs which aim to improve their functional language and communication skills, for example, Skinner's Verbal Behavior (VB) training programs or Picture Exchange Skills (PECS), American Sign Language (ASL), Princeton Child Development Institutes' Activity Schedules, just to mention a few. The goals of these programs are to enable autistic individuals to learn how to imitate and eventually acquire functional and more acceptable verbal and social behaviors.

A component of the normal communication and socialization process, is the ability to exhibit 'eye contact behavior' in social situations, a key deficit repertoire of autistic individuals and special needs individuals. Accordingly, it is the purpose of this disclosure to provide a system and method to train autistic and/or other individuals to develop 'social eye contact' skills.

Social eye contact behavior comes in many different flavors. The ability to socialize using 'eye contact behavior' takes on different dimensions. Examples of socialization dimensions for 'eye contact behaviors' include "joint attention" to objects in the environment, an antecedent condition for teaching verbal, auditory or other skills. Other factors and methods related to the subject include the shaping of eye ball movement, tracking and monitoring an individual's body movements as well as other body movement, monitoring the ability to communicate and manage remote devices like recorders, musical instruments and other electronic devices, allowing deaf and blind people to detect individuals in a social setting, playing recorded voices and requiring an autistic child to repeat the voices with proper eye contact behavior, and teaching language skills during eye contact behavior to achieve socialization skills and other and similar types of behaviors as described below.

The prior art has identified and described devices and systems that monitor 'eye movements', to be used as an input to a computer system, or to alert a wearer of specialized eyeglasses when fatigued, or for monitoring the safety of an individual. U.S. Pat. No. 6,959,109 describes a system for estimating the pose-angle of a picture or a person and its teachings are therefore incorporated by reference herein. Some of the prior art methods utilize specialized eyewear-glasses or just recording eye movements and gazes.

It is the purpose of this invention to train an individual to perform 'social eye contact' behavior.

In ordinary situations a 'social eye contact' event occurs when two or more individuals are having a conversation, or when an object becomes the focus of one or more individual's attention ("joint attention") or when two or more individuals are sending implicit signals without any conversation or speech, a signal to attend to one another, a mother signaling her child to follow, etc.

It is a general object of the WatchMe disclosure to provide a system and method that monitor and obtain qualitative and quantitative information about the eye contact habits of a subject being trained or interviewed. A further general object of the invention is to use such a monitoring system which also helps train the individual being monitored, by inducing him or her, for example, by providing certain rewards or by providing pleasant feedback and a positive response that induces the behavior of a monitored person to practice and seek communication while using appropriate eye contact behavior.

In accordance with one particular embodiment of the present disclosure, the system utilizes at least two pairs of eyeglasses, with the goal of the session being to train either two or more individuals to conduct a conversation with social eye contact or to cause two or more individuals to participate in a joint attention activity with various objects in the environment. Each eyeglass pair has either or both, transmitter and receiver capabilities. The transmitting and receiving protocol of each pair of glasses uses standard protocols like Infrared (IR), Radio Frequency (RF), Bluetooth, or WI-FI signaling. The receiving or transmitting mode of the pair of eyeglasses is determined by either a small remote hand held switch or by an on/off switch located on both sides of the eyeglasses. Either party wearing the eyeglasses can control the on/off signaling function of either pair of glasses. When a request for eye contact is made by the transmitting pair of eye glasses the receiving glasses can either reject or accept the contact. Once the contact is accepted the receiver will begin to produce a head movement in the direction of the signal. If the individual wearing receiving eye glasses makes a partial contact, the transmitting source can provide a primary or secondary reinforcer. The "reinforcer" can be the positive reinforcer or the negative reinforcer. For example, a positive reinforcement might play pleasant music to the listener upon fixing his or her gaze in the direction of the other person. A negative reinforcer may remove an annoying noise when the listener has properly turned her head towards the person addressing her. The transmitting source will, through a process of successive approximations, condition the receiving source to look in the right direction and begin a limited conversation. The receiver will know of a successful eye contact when the receiver's eyeglasses line-up with the transmitting signaling eye glasses and detects the transmitting signal from the sending eyeglasses. This is the moment when the handshaking protocol occurs.

Once an initial signal is sent by the transmitting eyeglasses and received by the receiving eyeglasses an event for a 'social eye contacting' is marked. The event is detected by one of the sensory modalities, either sight, sound, touch or smell signal. The signal sent by the sender of the message becomes a discriminative stimulus and marks the onset of a 'social eye contact' event to the receiver of the event. Once the receiver of the event receives the message, he will be exposed to a behavioral shaping program that will, through successive approximations, using primary and secondary reinforcers condition the wearer to look at the sender's eyes and proceed with phased dialogues and conversations.

If the social eye contact event consists of training an interaction with an object, e.g., a toy car, the object will have the capability of receiving and transmitting signals as well. The object will signal the receiving eye glasses for a request of an eye contacting event. When a request for eye contact is made by the transmitting object the receiving glasses can either reject or accept the contact. Once the contact is accepted, the receiver will begin to produce a head movement in the direction of the signal. If the individual wearing receiving eye glasses makes a partial contact with the object, the transmitting source can provide a primary or secondary reinforcer. The transmitting source will, through a process of successive approximations, condition the receiving source to look at the right direction. The receiver will know of a successful eye contact when the receiver's eyeglasses lines up with the transmitting signaling of the object and then walks over to the object to pick it up for at least, for example, 10 seconds. This is the moment when the handshaking protocol occurs.

If the social eye contact event consists of training two or more individuals to send implicit signals without any conversation or speech at least two pairs of eyeglasses will be used to train two or more individuals to conduct a conversation with social eye contact but no speech. Each pair has both a transmitter and receiver capability. The transmitting and receiving protocol of each pair of glasses uses standard protocols like Infrared (IR), Radio Frequency (RF), Bluetooth, or WI-FI signaling. The receiving or transmitting mode of the pair of eyeglasses is determined by either a small remote hand held switch or by an on/off switch located on both sides of the eyeglasses. Either party wearing the eyeglasses can control the on/off signaling function of either pair of glasses. When a request for eye contact is made by the transmitting pair of eye glasses the receiving glasses can either reject or accept the contact. Once the contact is accepted the receiver will begin to produce a head movement in the direction of the signal. If the individual wearing receiving eye glasses makes a partial contact, the transmitting source can provide a primary or secondary reinforcer. The transmitting source will, through a process of successive approximations, condition the receiving source to look in the right direction. The receiver will know of a successful eye contact when the receiver's eyeglasses line-up with the transmitting signaling eyeglasses.

A CPU and eye gazing application software monitors the quantitative elements of the eye contacting event of both transmitting and receiving eye glasses, for example the number of eye contact events, latency of eye contact event, the duration of the event, the rate of the events that occur over a specified time and the number of incorrect eye contact events and the fluency or strength of the eye contacting event. The system provides reports and graphs on these measures.

The system will enable the users to parameterize the amount of time required for the social eye contact events based on the type of social eye contact events; when two or more individuals are having a conversation, or when an object becomes the focus of an individual's attention or when two or more individuals are sending implicit signals without any conversation or speech. A general flow chart of the preferred embodiment appears in FIG. 14A.

Figure 14A:
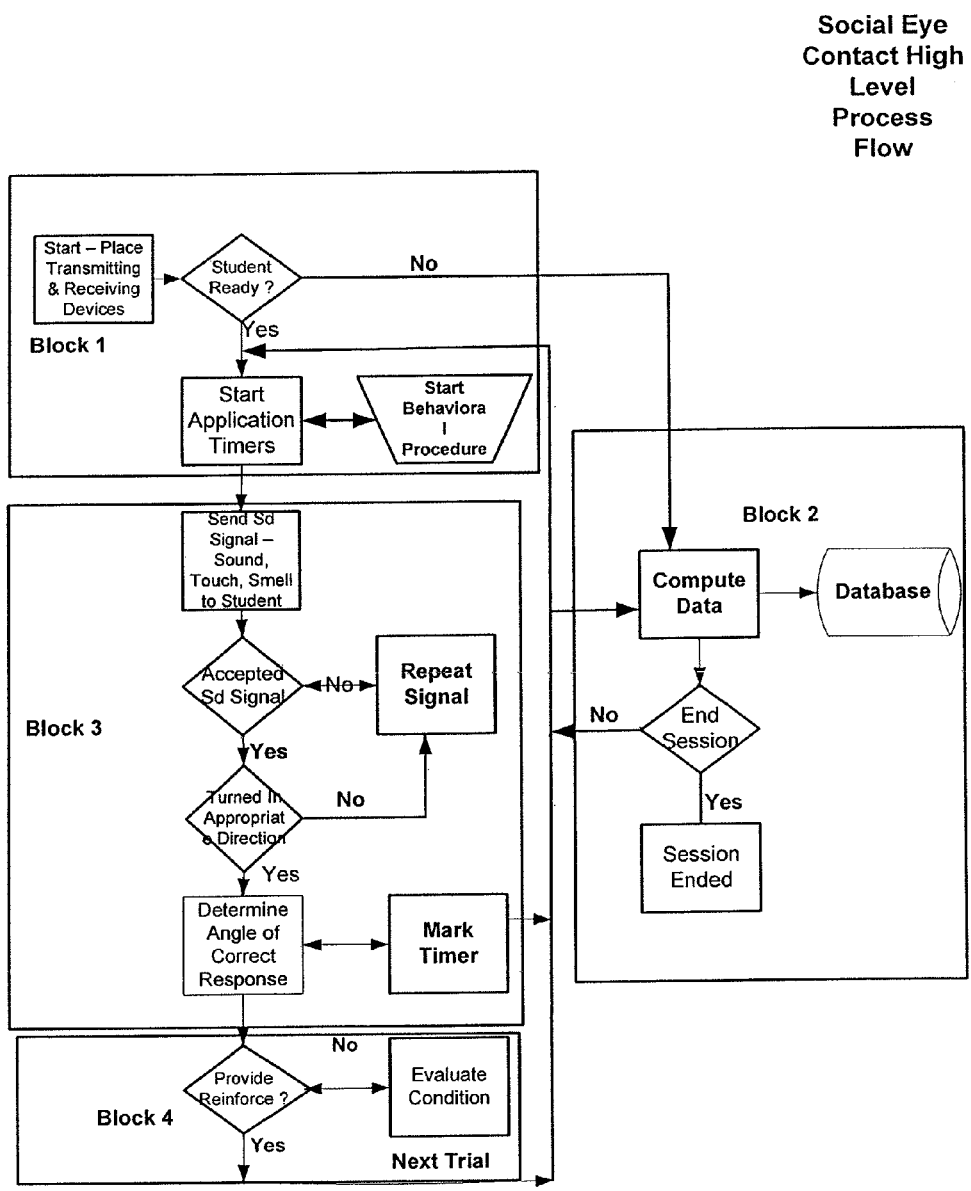
FIG. 14A is a block diagram of the WatchMe block diagram in the form of a high level process flowchart.

FIG. 14A is a high level description of the process flows involved in the WatchMe system. The invention takes many forms but can be composed of four basic building blocks as described in FIG. 14A.

In FIG. 14A, Block 1 describes the module for 'gaining a student's attention', scoring and recording the frequency and duration of the attention to the system. If a student's attention is gained the process will immediately move on to Block 3, the data collection, management and storing module and Block 2 is the 'training module'. If a student's attention is not attained the application based on the parameters defined will record and store the response and either terminate the session or start the application again. Block 1 includes a shaping procedure which allows the trainer through successive approximations to provide the conditions for either an external manual or system procedure to elicit the desired response.

Block 2 collects input from Block 1, Block 3 and Block 4. It collects the data from each block, manages the output to each block and provides various reports and graphs about the social eye contact behavior, for example the rate, frequency duration, latency and strength of the social eye contact behavior.

Block 3 identifies and describes the attainment and detection of a threshold of a discriminative stimulus (Sd). Discriminative stimuli (Sd) are stimuli that can affect either the Exteroceptors, small structures within the eye, ear, or the skin external to the organism, Interoceptors, tiny organs which lie mainly within the alimentary tract which are excited by internal stimuli or Proprioceptors which are located within the muscles. If social eye contact behavior occurs then the angle of the detection is recorded by the application and processed by Block 2 and either a primary, secondary, or social reinforcer is presented in Block 4.

In Block 4 the strength of the behavior and the reinforcer is evaluated. If there is an increase in the rate of the social eye contact behavior the application will continue to present the existing reinforcer, if the rate of the social eye contact behavior decreases then the application will suggest other historical and available reinforcers. Once the evaluation occurs the application will either continue to another trial as operationally defined in the application or end session.

If the social eye contact behavior does not occur then another Sd signal is presented and monitored.

Figure 14B:
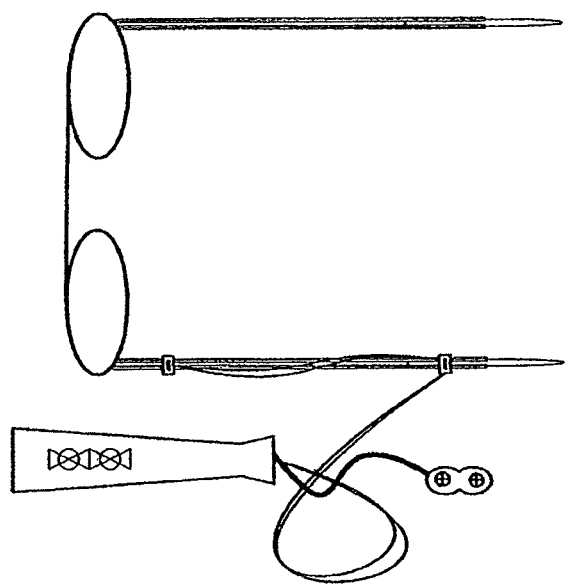
FIG. 14B is a photo of an eyeglass frame to which is utilized to support a receiver circuit.
Figure 14C:
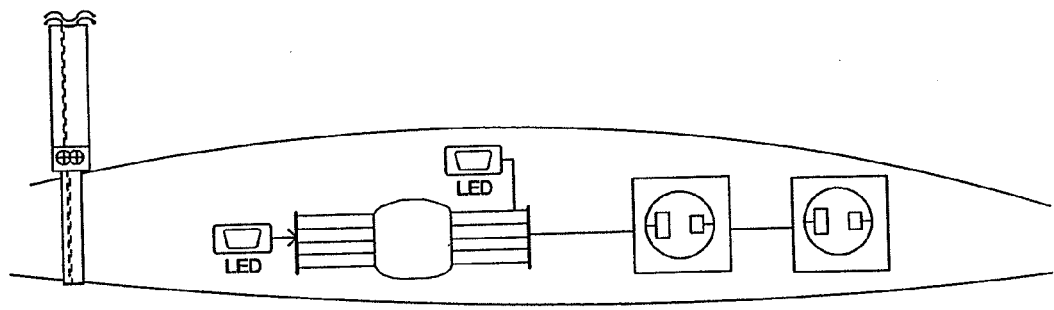
FIG. 14C is a child's transmitter circuit supported by an eyeglass frame.
Figure 14D:
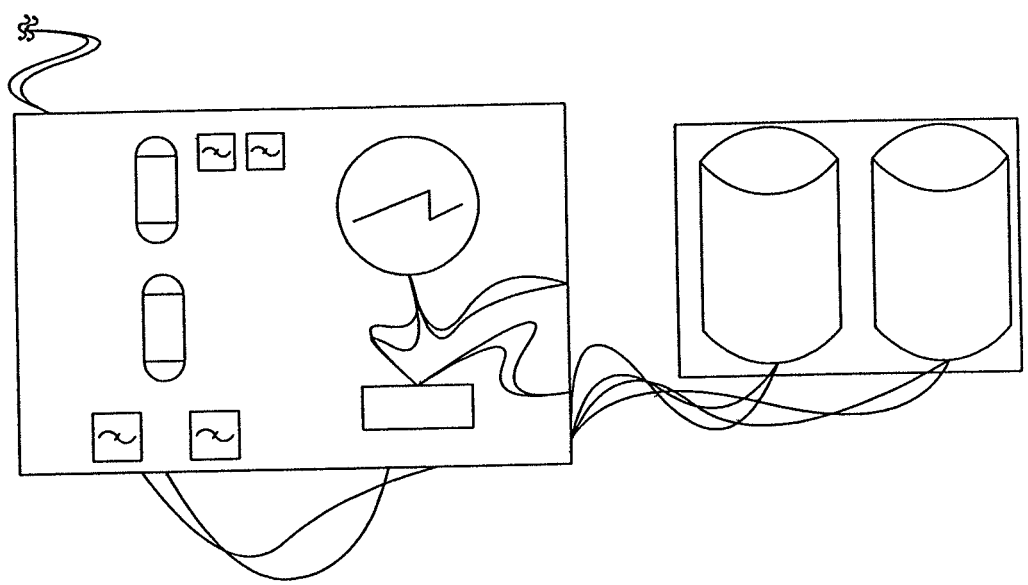
FIG. 14D is a photo of a circuit layout for the receiver of the trainer.
Figure 14E:
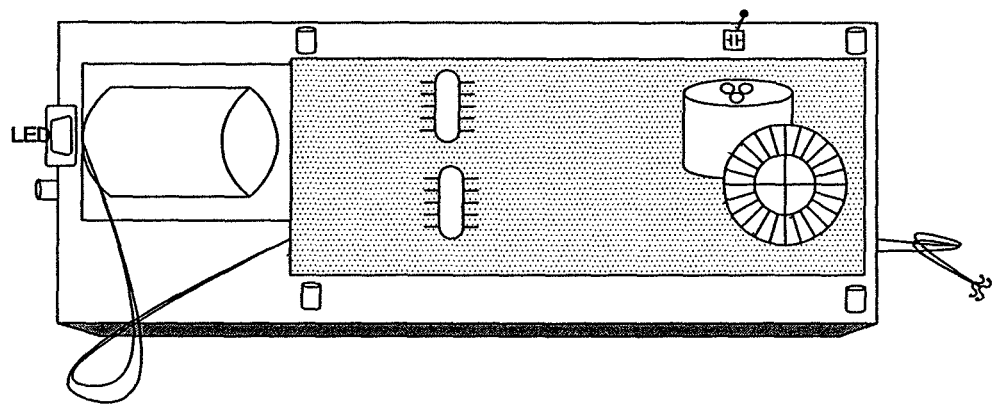
FIG. 14E illustrates a housing with a circuitry for the receiver of FIG. 14B.
Figure 14F:
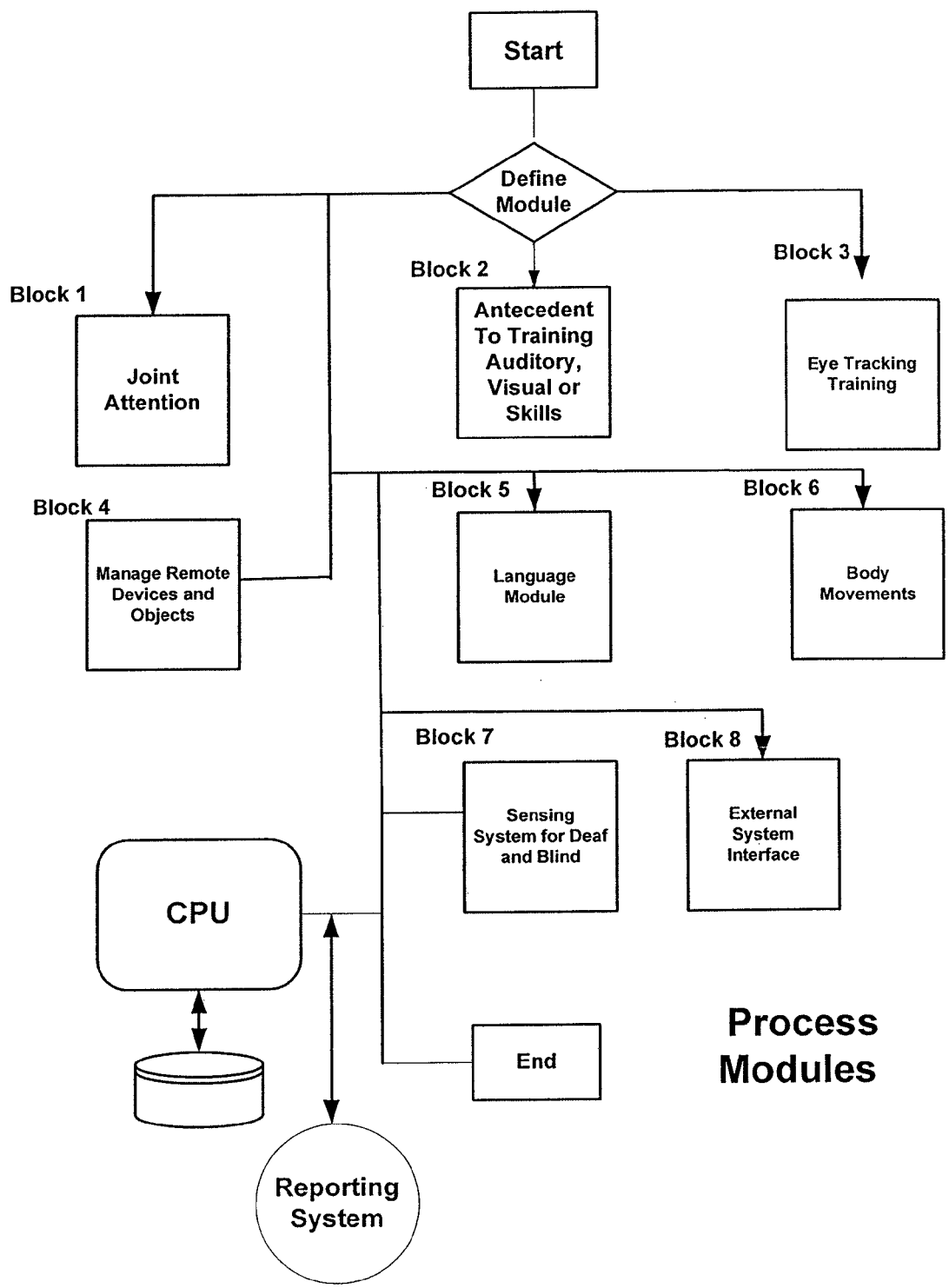
FIG. 14F is a process flowchart for the WatchMe system.

FIG. 14F describes the various processes which the WatchMe system addresses. The WatchMe application allows the user to select the process or processes that it wishes to address. WatchMe can select one or multiple processes to run.

When WatchMe is started there are various options and functions of 'social eye contact behavior' that can be selected. Below is a description of some of these application modules presented in the various blocks of FIG. 14F.

Block 1 defines a joint attention procedure. The joint attention procedure requires that the student and teacher interact with an object in the environment. WatchMe detects when the teacher and student are both looking at an object. The object in the environment has a receiver module and will only stop the emission of an aversive stimulus or produce a reinforcing stimulus if it detects two concurrent signals being emitted from the transmitting devices. If it detects such signals either the aversive stimuli will cease or a reinforcing stimulus will appear. WatchMe will then produce the appropriate graphs and reports about the events.

Block 2 defines a social eye contact event in which a social eye contact behavior is an antecedent condition for either training an auditory, visual or skills training procedure. The social eye contact event occurs when a student and teacher have their heads aligned towards each other so that there is a moment when the student and teacher recognize each other. Once this social eye contact event occurs a request is initiated by the teacher to either perform a skill, e.g., 'It's time to brush teeth', or to listen to directions like, 'It's time to eat supper' or visual training activity like 'Would you like to play ball?' In each one of these activities the social eye contact is required to initiate another activity. When the social eye contact event and the training activity occur in any of the above situations then either the termination of the aversive stimulus occurs or the insertion of a reinforcing stimulus will be presented. WatchMe will then produce the appropriate graphs and reports about the events.

Block 3 allows not only the monitoring of social eye contact behavior but also control the position of the eye. The eye tracking module requires that WatchMe detect social eye contact event occurring when a student and teacher have their heads aligned towards each other so that there is a moment when the student and teacher recognize each other. Once this social eye contact event occurs the receiver module will only stop the emission of an aversive stimuli or produce and reinforcing stimulus if WatchMe detects that the eye is in a certain position relative to the teacher. If it detects such a signal either the aversive stimuli will cease or a reinforcing stimulus will appear. WatchMe will then produce the appropriate graphs and reports about the events.

Block 4 allows WatchMe to interact with remote devices. The student is wearing a transmitting device and the object in the environment has the receiving device. If the student's transmitting device is detected by the object in the environment, e.g., a play toy truck, and the application requires the student to pick up the object in the environment, then either the emission of an aversive stimulus occurs or a reinforcing stimulus is presented. If it detects that the student has, e.g., picked up the toy, then either the aversive stimuli will cease or a reinforcing stimulus will appear. WatchMe will then produce the appropriate graphs and reports about the events.

Block 5 is a language and verbal behavior training module. The language and verbal behavior training module requires that the student and teacher produce social eye contact behavior as well as have the student imitate verbal or language behavior. The social eye contact event occurs when a student and teacher have their heads aligned towards each other so that there is a moment when the student and teacher recognize each other. Once this social eye contact event occurs a language module appears. The language module requires that the student imitate the verbal behavior or language emitted. If the application requires that both social eye contact behavior occur and certain words to be spoken, then once this social eye contact event occurs, the receiver module will only stop the emission of an aversive stimuli or produce and reinforcing stimulus if WatchMe detects that certain verbal or language behavior was emitted. If it detects such an event, then either the aversive stimuli will cease or a reinforcing stimulus will appear. WatchMe will then produce the appropriate graphs and reports about the events.

Block 6 requires a social eye contact behavior as well as detection of certain body movements, e.g., a smile, certain body gestures or other similar body movement. Once the social eye contact event occurs when a student and teacher have their heads aligned towards each other so that there is a moment when the student and teacher recognize each other. Once this social eye contact event and certain body movements occur, the receiver module will stop the emission of an aversive stimuli or produce and reinforcing stimulus if WatchMe detects that certain body movement behavior was emitted. If it detects such an event, then either the aversive stimuli will cease or a reinforcing stimulus will appear. WatchMe will then produce the appropriate graphs and reports about the events.

Block 7 is applied to either deaf or blind people. This module allows the deaf or blind person to sense the occurrence of social eye contact behavior. The social eye contact behavior occurs when a student, the blind or deaf individual and teacher have there heads aligned towards each other. Once this social eye contact event occurs the receiver module will only stop the emission of an aversive stimuli or produce and reinforcing stimulus if WatchMe detects that the heads are aligned. If it detects such an alignment either the aversive stimuli will cease or a reinforcing stimulus will appear. WatchMe will then produce the appropriate graphs and reports about the events.

Block 8 is an interface to other educational or behavioral systems that want to interface to WatchMe. WatchMe will either accept or transmit programs or data through this interface. The purpose of this interface is to allow various programs to be used in conjunction with social eye contact behavior an expand the acquisition of social eye contact behavior in various circumstances.

With further reference to the figures, in FIG. 14B are shown the portions of the eyeglass frame which supports a wide angle receiver attached to the right temple, ear piece. This receiver is connected by a wire to circuitry described in other figures.

In FIG. 14C is shown the slave, or child transmitter circuit which is similarly connected to an eye frame and comprises a self contained package with two batteries as shown and with an LED infrared transmitter shown at the left of the figure. In a typical application, this module is encased in its own housing and attached by clips or glued to the right hand ear piece of the eye glasses.

In FIG. 14D is shown the circuitry which interfaces with the wide angle receiver of FIG. 14B. This receiver circuitry is further shown packaged in a housing in FIG. 14E. This housing contains batteries for powering the circuit, a tone volume adjustment and a toggle switch which provides on/off functions.

Figure 14G:
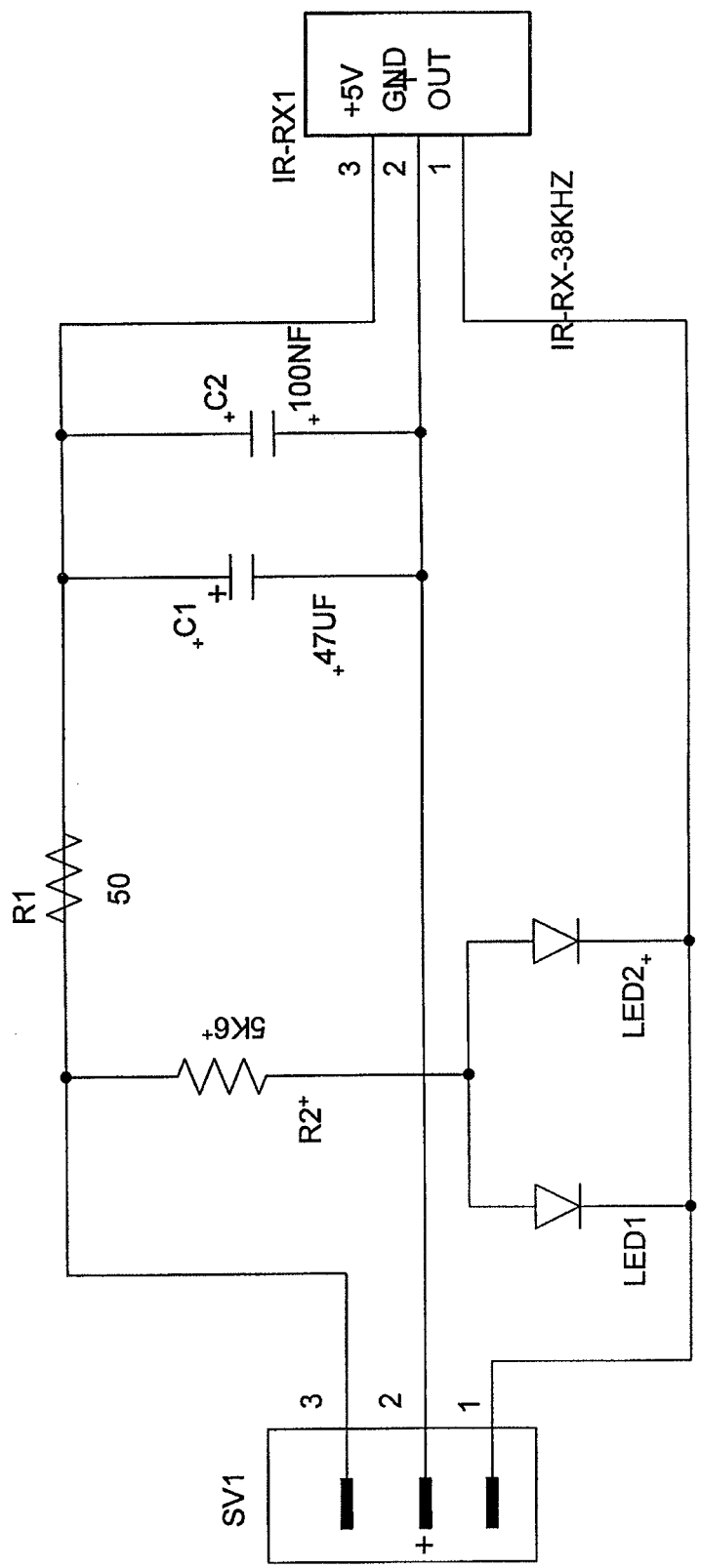
FIG. 14G is a circuit diagram for an infrared wide receiver.
Figure 14H:
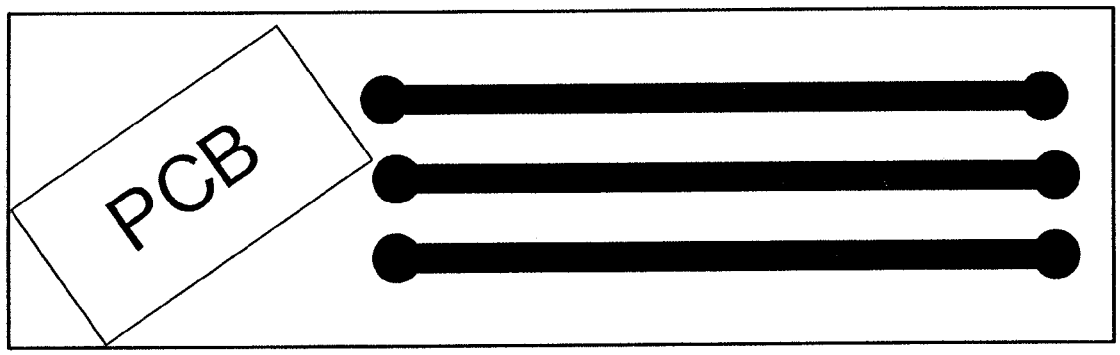
FIG. 14H is a circuit layout for the circuit of FIG. 14G.
Figure 14I:
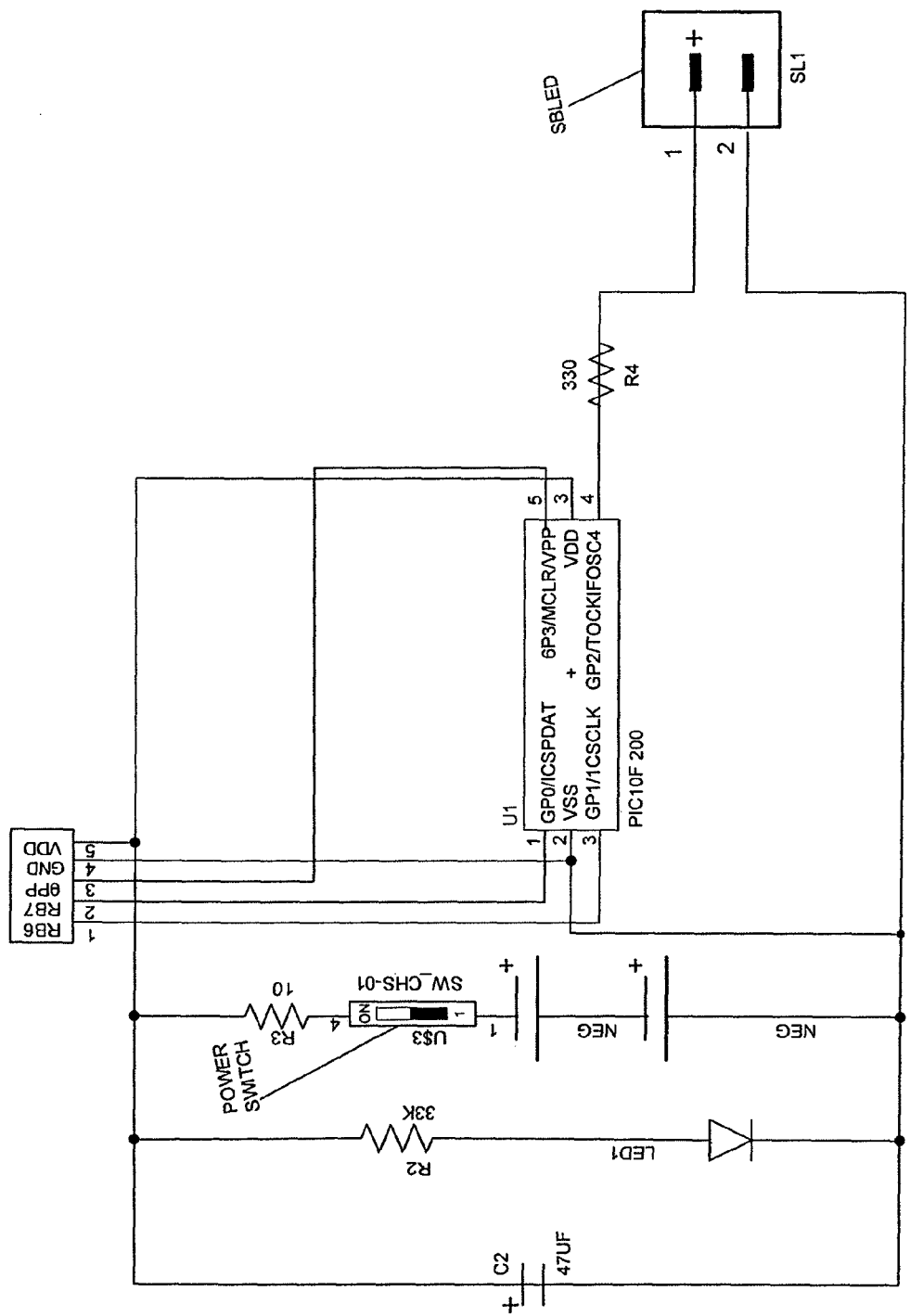
FIG. 14I is a circuit diagram for an infrared, narrow angle transmitter.
Figure 14J:
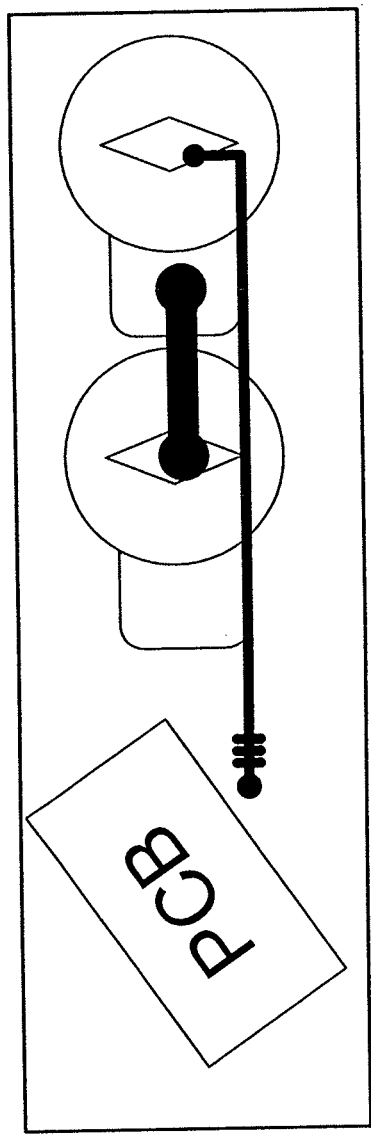
FIG. 14J is a circuit layout diagram for the circuit of FIG. 14I.

More detail about this transmitter and receiver complementary circuits are shown in FIG. 14G and FIG. 14H as well as in FIG. 14I and FIG. 14J. In FIG. 14G, SV1 represents the wide angle receiver which provides an output signal at pin 1 which is the "out" pin at the connector identified as IR-RX1. The two LEDs light up when a signal becomes active and allow the child to notice that he or she has turned their head toward the receiver. These LEDs are optional devices. The layout of the circuit in FIG. 14G is shown in FIG. 14H.

FIG. 14I shows the narrow angle transmitter which is located on the eye glass frame shown in FIG. 14C. Here the part marked as SL1 is a two terminal device which represents the narrow angle transmitter which outputs an infrared beam of approximately 8 degrees. A narrow beam can comprise a beam from 2 degrees to even 10 or even 20 degrees wide. This transmitter device is driven by a micro-controller that is programmed to cause the transmitter to issue only burst signals of low duty cycle to cause the battery to last for quite a long time, on the order of 40 hours. The micro-controller can be a microchip model PIC10F200 IR LED. Note that the receiver in FIG. 14G may be a Fairchild model QEC122 (8 degree beam) IR, wide angle receiver. Also included is a Sharp model GP1UX511US. Regardless, the transmitter is powered by two batteries as shown and it includes and on/off power switch and the capacitor and resistor as shown. The layout of the circuit in FIG. 14I is shown in FIG. 14J.

As a general proposition, it should be noted that the receiver and transmitter of the type described above need not be mounted to an eye glass frame. For example, they can be attached to an audio headphone style holder, which is worn by the child and/or the teacher. Or they can be attached by any other means to the head of the person. Moreover, the headphone can be used to pipe either positive reinforcement, e.g., pleasant music and the like to the ears of the child or, alternatively, negative stimulant such as an unpleasant noise, when the child gazes away from the teacher. As a general proposition, other means can be utilized to determine that the student or child is turning his or her head toward the teacher or trainer, for example, as described in the aforementioned U.S. patent. Other means might be utilized to determine the angular position of the child, for example, GPS techniques and the like. For example, various receivers may be located in a room in which training is administered and a triangulation system attached to the child's head may be utilized to beam signals that allow the determining his or her head position or orientation relative to that of the teacher or the trainer.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A system for encouraging a developmentally challenged patient to maintain eye contact with a human trainer, during verbal training communications, the system comprising:
    a first receiving device worn by the patient, located in a room in which training is administered, and configured to provide a direction indication representative of a direction to which the head of the patient is facing;
    a second transmitting device, worn by the human trainer located in the room, and configured to sense the direction indication from the first device via an alignment degree between the first device and the second device; and
    a circuit which outputs a reinforcement stimulation to the patient, to encourage the patient to orient her head toward the head of the trainer, in a manner which helps establish eye contact with the trainer.

2. The system of claim 1, wherein the first device is at least one of a transmitter and a receiver and wherein the second device is at least one of a receiver and transmitter, respectively, and wherein one of the first and second devices issues an output when the first device and the second device are generally directed toward one another.

3. The system of claim 2, wherein the first device is a transmitter and the second device is a receiver, and
    wherein the first device is a narrow beam infrared transmitter.

4. The system of claim 1, wherein the circuit outputs a negative, unpleasant sound when the patient does not orient her head toward the trainer.

5. The system of claim 1, wherein the circuit outputs a pleasant sound when the patient orients her head toward the trainer.

6. The system of claim 1, wherein at least the first device is supported on a eyeglass frame.

7. The system of claim 1, wherein the first device is self contained.

8. The system of claim 1, including a communication system between the first device and the second device using one of a standard protocol selected from the group consisting of Infrared (IR), Radio Frequency (RF), Bluetooth, and WI-FI signaling.

9. The system of claim 1, including a processing system comprising a CPU executing a computer program which is configured to monitor quantitative elements of eye contacting events.

10. The system of claim 9, wherein said quantitative elements comprise at least one of a plurality of eye contact events that include latency periods of eye contact events, durations of events, rates of events occurring over a specified time, numbers of incorrect eye contact events, and fluency or strength of eye contact events.

11. The system of claim 9, wherein said CPU includes a facility that is configured to provide reports and graphs of said quantitative elements.

12. The system of claim 1, wherein said system comprises a facility that is configured to interact with remote devices.

13. The system of claim 9, wherein said CPU includes a facility that is configured to output negative stimulations to discourage predetermined types of conduct.

14. The system of claim 1, further including a facility that is configured to detect predetermined body movements.

15. A method for encouraging a developmentally challenged patient to maintain eye contact with a human trainer during verbal training communication sessions, said method comprising:
    providing the patient with a first receiving device, located in a room in which training is administered, and fitting it to the head of the patient and configured to provide a direction indication representative of a direction to which the head of the patient is facing;
    providing the human trainer with a second transmitting device, worn by the human trainer located in the room, and configured to sense the direction indication from the first device via an alignment degree between the first device and the second device; and
    reinforcing communication with the trainer by stimulating the patient with a circuit that produces an output that encourages the patient to orient the patient's head toward the head of the trainer, in a manner which promotes eye contact with the trainer.

* * * * *